United States Patent [19]
Malis et al.

[11] Patent Number: 5,318,563
[45] Date of Patent: Jun. 7, 1994

[54] BIPOLAR RF GENERATOR

[75] Inventors: Jerry L. Malis, King of Prussia, Pa.;
Leonard I. Malis, Queens, N.Y.;
Robert R. Acorcey, Cherry Hill, N.J.;
Harry E. Klaus, Bryn Mawr; David
L. Solt, Fort Washington, both of n,
Pa.; Frank DiJoseph, Atco, N.J.

[73] Assignee: Valley Forge Scientific Corporation, Oaks, Pa.

[21] Appl. No.: 893,308

[22] Filed: Jun. 4, 1992

[51] Int. Cl.⁵ .............................................. A61B 17/39
[52] U.S. Cl. ................................... 606/38; 606/34; 606/37
[58] Field of Search ................. 606/32–40; 128/419 R, 419 B

[56] References Cited

U.S. PATENT DOCUMENTS

| | | |
|---|---|---|
| 4,590,934 | 5/1986 | Malis et al. .................. 128/303.14 |
| 4,716,897 | 1/1988 | Noguchi et al. ..................... 606/37 |
| 4,727,874 | 3/1988 | Bowers et al. ..................... 606/37 |
| 4,903,696 | 2/1990 | Stasz et al. ........................ 606/37 |
| 4,934,377 | 6/1990 | Bova et al. ........................ 606/34 |

*Primary Examiner*—Stephen C. Pellegrino
*Assistant Examiner*—Michael Peffley
*Attorney, Agent, or Firm*—Panitch Schwarze Jacobs & Nadel

[57] ABSTRACT

An electrosurgical bipolar RF generator apparatus includes a bipolar electrode. An aperiodic sequence of uniform width bursts of a high frequency signal are electronically synthesized. Substantially identical decaying amplitude envelopes are impressed on the bursts of the high frequency signal. Each of the envelopes has a predetermined rate of change from a preselected initial amplitude. The impressed bursts of the high frequency signal are applied to the electrode. The electrical apparatus operates in a cut mode or a coagulation mode. The apparatus includes a power supply for providing a variable DC voltage, a short circuit detect circuit for detecting a short circuit at the bipolar electrode, and an open circuit detector for detecting an open circuit at the bipolar electrode.

17 Claims, 34 Drawing Sheets

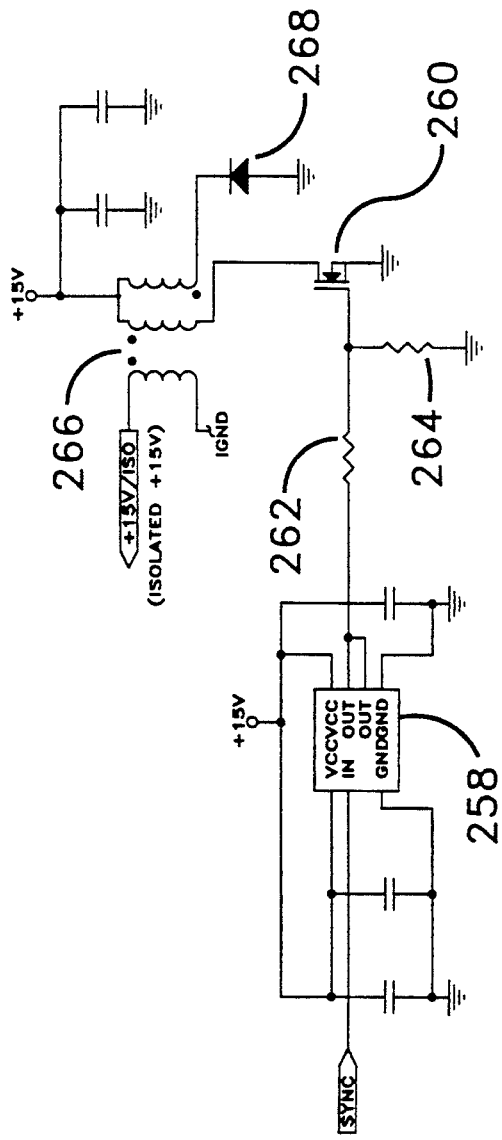
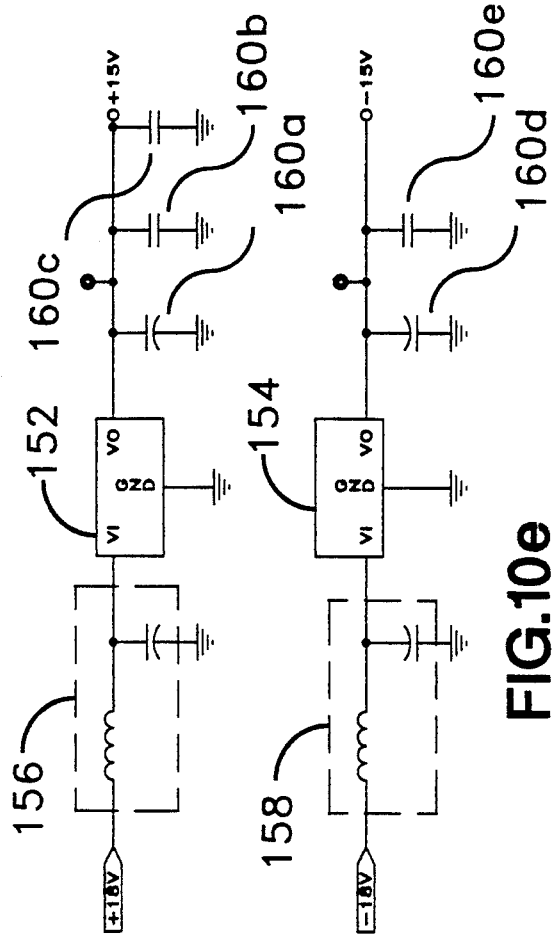
FIG.10d
FIG.10e

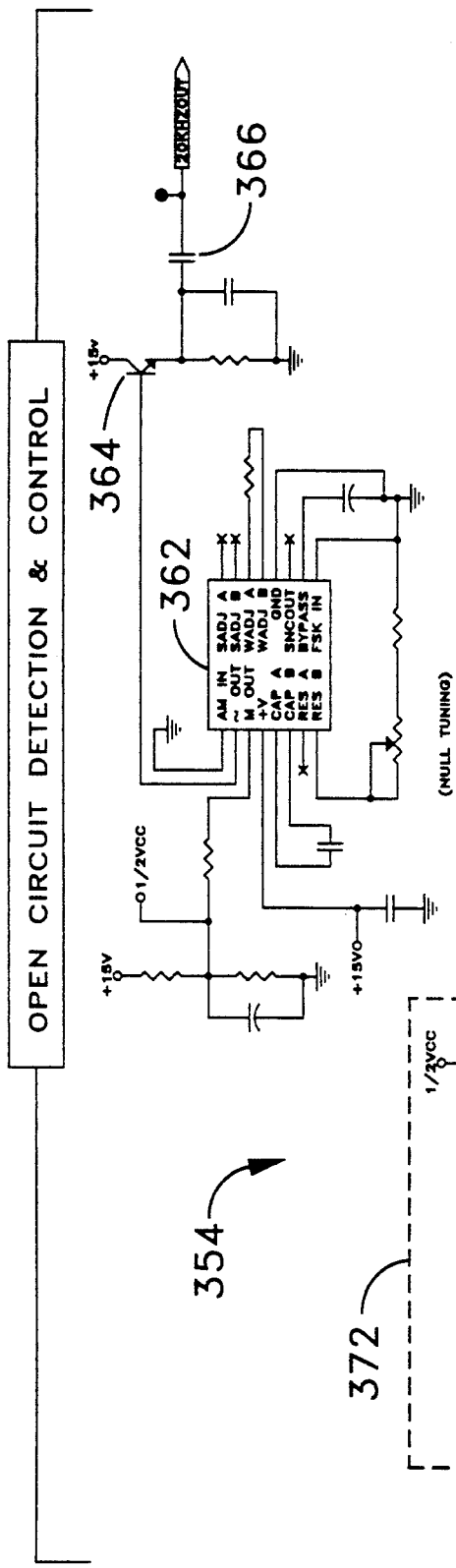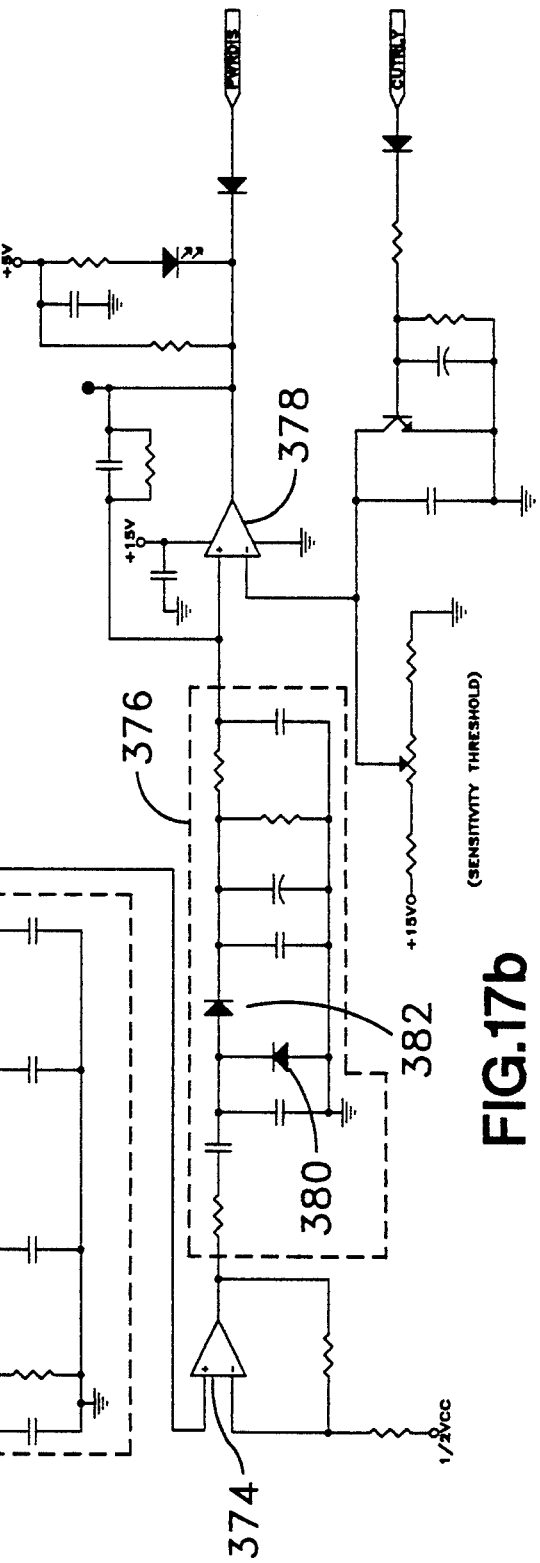
FIG.17a
FIG.17b

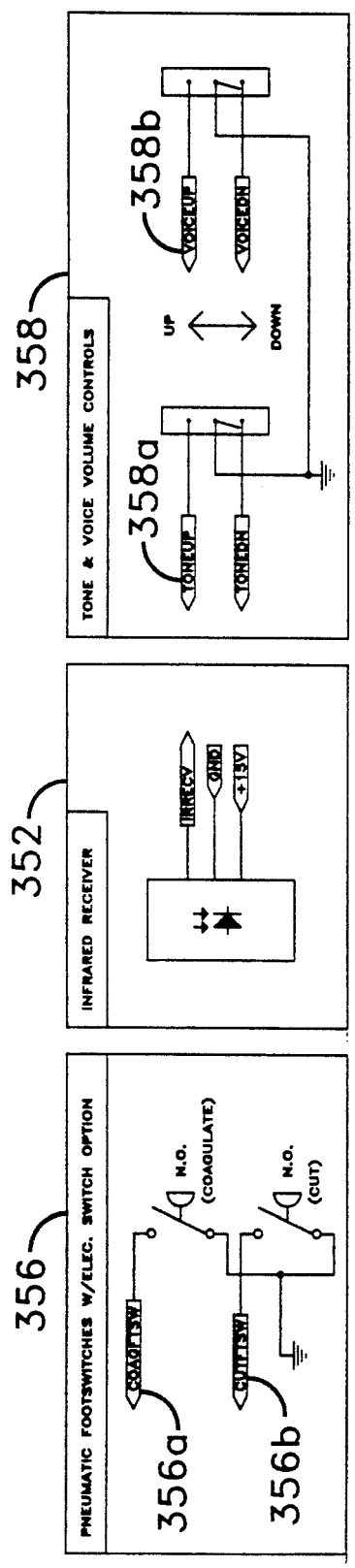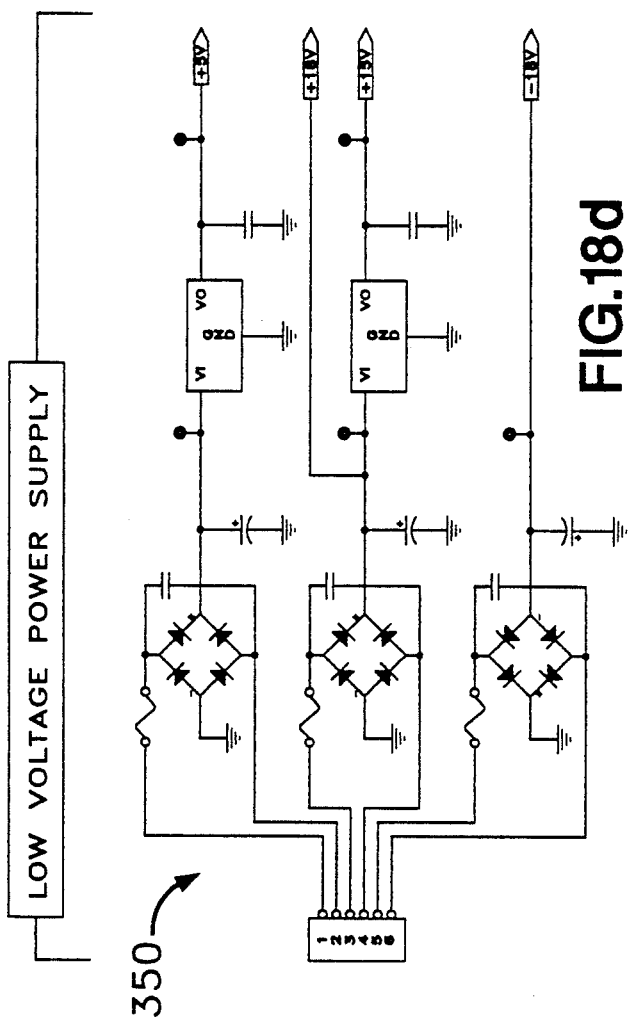
FIG.18c
FIG.18b
FIG.18a
FIG.18d

BIPOLAR RF GENERATOR

BACKGROUND OF THE INVENTION

The present invention is directed to a bipolar RF generator for an electrosurgical cutter/coagulator system and, more particularly, to a bipolar RF generator for producing a cutting waveform or a coagulating waveform having an aperiodic sequence of damped RF bursts.

Most electrosurgical systems which are employed to cut or coagulate tissue are based on the theory of molecular resonance. When living tissue is resonated within a given range of frequencies, typically 250 KHz to 16 MHz, the molecules within the tissue resonate and cause the tissue to be destroyed. The energy provided to cut the tissue is normally transmitted in the form of a controlled sinusoidal wave which causes relatively constant destruction to the tissue.

When tissue is to be coagulated, it is preferable that the tissue be resonated to a point where tissue destruction is initiated, but that the tissue destruction be controlled or limited. Most prior art systems generate a damped sinusoidal wave which causes tissue destruction to commence, but allows the tissue to anneal resulting in tissue coagulation.

Many prior art coagulators use periodic damped sinusoidal waves to coagulate the tissue. However, there is a strong tendency for a second resonant frequency to develop as the damped sinusoidal waves overlap. This produces an uncontrolled sinusoidal signal which could ultimately destroy the tissue.

There is a need for an RF generator which transmits bursts of frequencies aperiodically to form damped sinusoidal waves. It would also be beneficial to be able to shift the time domain over which the frequency bursts occur to prevent the repetition of frequency patterns from occurring in future frequency bursts.

SUMMARY OF THE INVENTION

Briefly stated, the present invention is directed to an electrosurgical bipolar RF generator apparatus comprising a bipolar electrode, means for electronically synthesizing an aperiodic sequence of uniform width bursts of a high frequency signal, and means for impressing substantially identical decaying amplitude envelopes on said bursts of a high frequency signal. Each of the envelopes have a predetermined rate of change from a preselected initial amplitude. The apparatus further includes means for applying said impressed bursts of the high frequency signal to the electrode. The electrosurgical apparatus operates in a cut mode or a coagulation mode. A first improvement to the apparatus comprises a power supply for providing a variable DC voltage, a coagulation waveform generator for receiving and modulating said DC voltage, signal driving means for driving the flow of the modulated DC voltage at a predetermined rate, amplifying means for receiving and amplifying said modulated DC voltage, said amplifying means comprising a plurality of drivers which are alternately driven to produce a predetermined voltage level having a predetermined impedance level, converting means for converting the alternately driven plurality of drivers and modulated DC voltage to an amplified RF signal, and output means for identifying whether the amplified RF voltage signal is a cut signal or a coagulation signal as determined by an impedance level requirement, the output means providing impedance matching between the amplified RF voltage signal and the bipolar electrode.

A second improvement comprises a high voltage power supply. The high voltage power supply comprises a voltage source which generates an AC voltage signal, converting means for converting the AC voltage signal to a DC voltage signal, electronic switching means for receiving the DC voltage signal, a flyback transformer for receiving the DC voltage signal when the electronic switching means is conducting, the flyback transformer ramping linearly while the electronic switching means is conducting, reference signal means for generating a reference voltage signal, said reference means corresponding to a desired output voltage signal, comparing means for comparing the ramped DC voltage signal from the flyback transformer with said reference voltage signal, said comparing means determining if said ramped DC voltage signal exceeds said reference voltage signal, control means for controlling said ramped DC voltage signal from said flyback transformer such that said ramped DC voltage signal is prevented from exceeding said reference voltage signal, said control means further preventing said desired output voltage signal from exceeding said referenced voltage signal.

A third improvement comprises a short circuit detect circuit. The short circuit detect circuit comprises current sensing means for sensing current flowing through the bipolar electrode when the electrosurgical apparatus is in a coagulation mode, voltage converting means for converting the sensed current into a voltage signal, detecting means for detecting the voltage signal and for determining if the detected voltage signal exceeds the predetermined voltage level, power disabling means for disabling the flow of current to the bipolar electrode when the detected voltage signal exceeds the predetermined voltage level, timing means for measuring the detected voltage signal at predetermined periodic time intervals, and restoring means for restoring power to the bipolar electrode when the detected voltage signal is less than the predetermined voltage level.

A fourth improvement also comprises a short circuit detect circuit. The short circuit detect circuit comprises current sensing means for sensing current flowing through the bipolar electrode when the electrosurgical apparatus is in a cut mode, voltage converting means for converting the sensed current into a voltage signal, detecting means for detecting the voltage signal and for determining if the detected voltage signal exceeds a predetermined voltage level, power disabling means for disabling the flow of current to the bipolar electrode when the detected voltage signal exceeds a predetermined voltage level, timing means for measuring the detected voltage signal at predetermined periodic time intervals, and restoring means for restoring power to the bipolar electrode when the detected voltage signal is less than the predetermined voltage level.

A fifth improvement comprises an open circuit detect circuit. The open circuit detect circuit includes a waveform generator for producing a high frequency sinusoidal signal, buffering means for buffering the sinusoidal signal, voltage detecting means for detecting an output voltage signal at the bipolar electrode, comparing means for comparing the output voltage signal sensed at the bipolar electrode with a threshold voltage, impedance means for impeding the flow of the audio signal if the output voltage signal from the bipolar electrode exceeds the threshold voltage, and power disabling means for disabling power to the bipolar electrode when the threshold voltage is exceeded, wherein said disabling power is removed when the DC voltage signal no longer exceeds the threshold voltage.

BRIEF DESCRIPTION OF THE DRAWINGS

The foregoing summary, as well as the following detailed description of a preferred embodiment, will be better understood when read in conjunction with the appended drawings. For the purpose of illustrating the invention, there is shown in the drawings an embodiment which is presently preferred, it being understood, however, that the invention is not limited to the specific methods and instrumentalities disclosed. In the drawings:

FIGS. 10a-10e are circuit schematics of portions of the high voltage power supply of FIG. 9;

FIGS. 17a and 17b are a circuit schematic of portions of an open circuit detect circuit of the bipolar RF generator of FIG. 1;

FIGS. 18a-18d are general block diagrams of portions of the circuits contained on the mother board of the bipolar RF generator of FIG. 1;

DETAILED DESCRIPTION OF THE INVENTION

Figure 1:
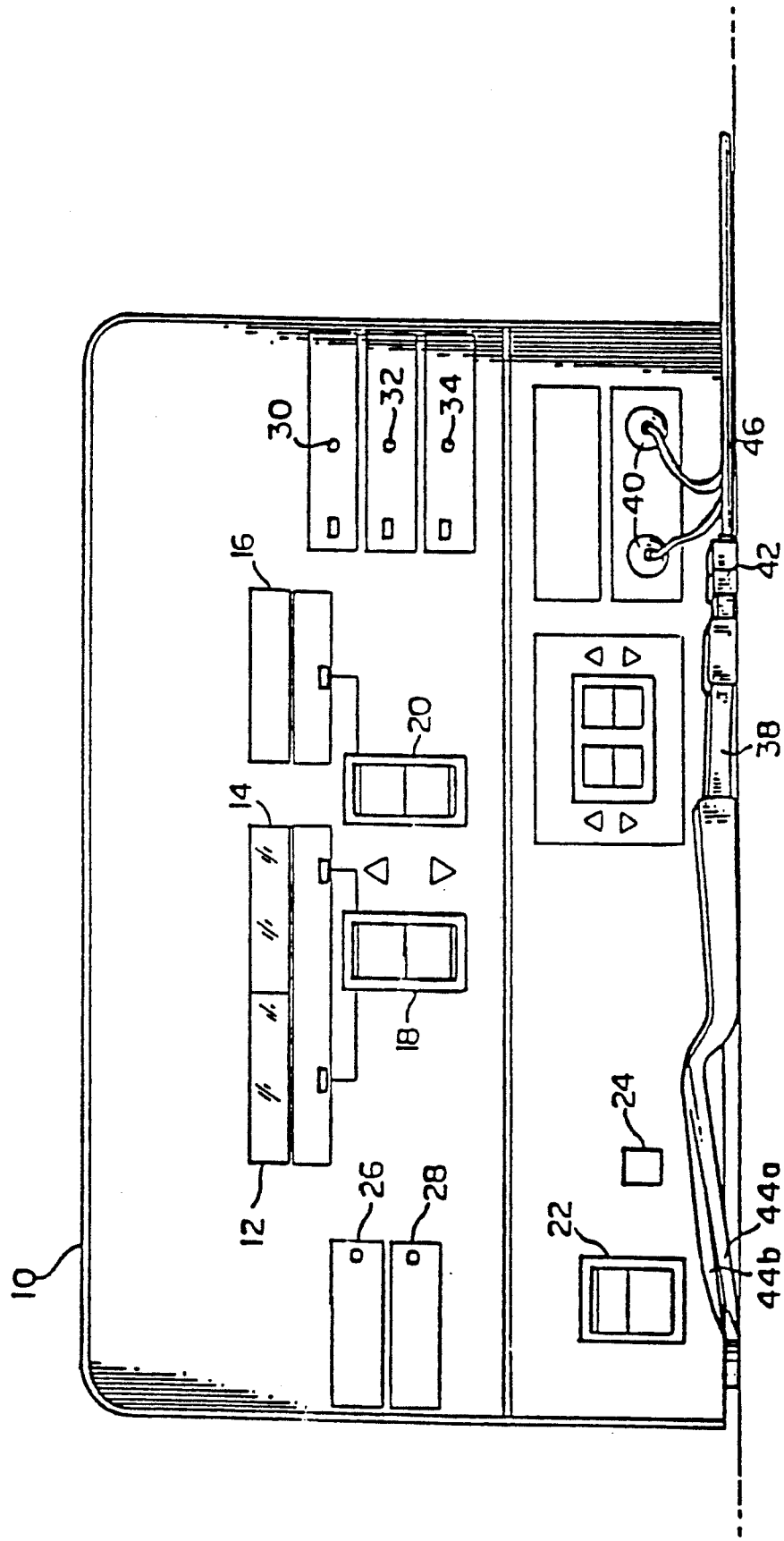
FIG. 1 is a view of a front panel of a bipolar RF generator in accordance with the present invention.

Referring to the drawings wherein like numerals indicate like elements throughout, there is shown in FIG. 1 a front panel 10 of a preferred embodiment of a bipolar RF generator in accordance with the present invention. The front panel 10 includes three numeric, preferably LED displays 12, 14, 16. The first LED display 12 displays the power output from the RF generator when operating in a cut mode. The second LED display 14 displays the power output from the RF generator when operating in a microcut mode. The third LED display 16 displays the power output from the RF generator during a coagulation or a coag mode of operation. For each of the three displays 12, 14, 16, the power output may be expressed either in watts or Malis units. A Malis unit is a reference term used to provide a repeatable indication of the output power which avoids the implied exactness of watts terminology which cannot be obtained with a load that varies in impedance which is typical with electrosurgery. Operation in the cut mode, the microcut mode or the coag mode is operator selectable by manipulating a foot pedal switch (not shown). The selected mode of operation can be announced by an unique mixture of tones as will be described in detail hereinafter.

A pair of up/down switches 18, 20 electrically control the increasing or the decreasing of the power output level of the RF generator. The first up/down switch 18 electrically controls the output power generated during operation in the cut mode and the microcut mode. The change in the power level is displayed by the cut LED display 12 and the microcut LED display 14, respectively. The second up/down switch 20 electrically controls the output power generated during operation in the coag mode. The numeric change in the power level is displayed by the coag LED display 16. In the preferred embodiment, the up/down switches 18, 20 are preferably rocker switches. However, it is to be understood by those skilled in the art that thumb wheel switches, detent switches or any other type of switches could be used.

An on/off switch 22 is located on the lower portion of the front panel 10 to control power being supplied to the RF generator. The on/off switch 22 may include an indicator light which is illuminated when the switch is on and power is being supplied to the RF generator. Adjacent to the on/off switch is a remote control window 24 for receiving infrared control signals from a remote control device (not shown) for remote operation of the RF generator.

Immediately above the on/off switch 22 are a pair of push button switches 26, 28. The first switch 26 is a coag reset switch which, when actuated, resets the coag power to an initial, predetermined power level. The second switch 28 is a cut reset switch which when actuated, resets the cut and/or microcut power to an initial, predetermined power level. The initial cutting or coagulating level is selected to be 35 Malis units.

A plurality of other LEDs on the front panel 10 indicate various other operational features of the RF generator. An irrigation LED 30 indicates when irrigation is being used. A power output LED 36 indicates when RF output power is applied. A mute LED 32 indicates when the generator's voice system has been muted. A watts LED 34 indicates that the numeric displays 12, 14 and 16 are displaying the power output in watts.

An electrosurgical instrument, such as forceps or a bipolar surgical pen 38 is connected to the bipolar RF generator by a cord 46 connected to an output adaptor 40. The bipolar surgical pen 38 typically comprises a generally elongated insulated handle 42 which is sized to be easily gripped by a surgeon or other user and which contains a pair of spaced electrodes 44a, 44b. The electrodes 44a, 44b are preferably parallel to one another and partially extend from one end of the bipolar pen 38. The electrodes 44a, 44b are each of opposite polarity such that one electrode is positively charged and the other electrode is negatively charged, alternately, during use. The electrodes 44a, 44b can be of varying diameters, shapes and thicknesses depending upon the particular use for which the electrodes 44a, 44b are to be applied. Details of the structure of various types of surgical pens may be obtained by reference to copending U.S. patent application Ser. No. 07/735,138 filed Jul. 24, 1991 and entitled "Bipolar Surgical Pen," which is incorporated herein by reference.

In operation, energy is generated by the RF bipolar generator and is transmitted to the bipolar surgical pen 38 via the adaptor 40. The energy is conducted from the adaptor 40 to the electrodes 44a, 44b via a connecting means 46 such that during use each electrode is oppositely charged. The energy is transmitted to the tips of the electrodes 44a, 44b extending from the bipolar pen 38. The proximity of the parallel spaced electrodes 44a, 44b causes a voltage to be generated between the tips of the electrodes 44a, 44b. The electrodes 44a, 44b are strategically spaced to provide an optimum voltage suitable for cutting and/or coagulating tissue. When the tips of the electrodes 44a, 44b are placed proximate to the tissue, the voltage generated by the electrodes 44a, 44b causes the tissue to resonate and be destroyed. Because the bipolar surgical pen 38 can be easily manipulated, a surgeon or other user can conveniently control the amount of tissue which is cut and/or coagulated. The tips of the electrodes 44a, 44b of the bipolar surgical pen 38 may comprise different shapes to allow for different medical applications to be applied to the tissue, such as, but not limited to, coagulation, cutting, dissection, separation and removal.

Figure 2:
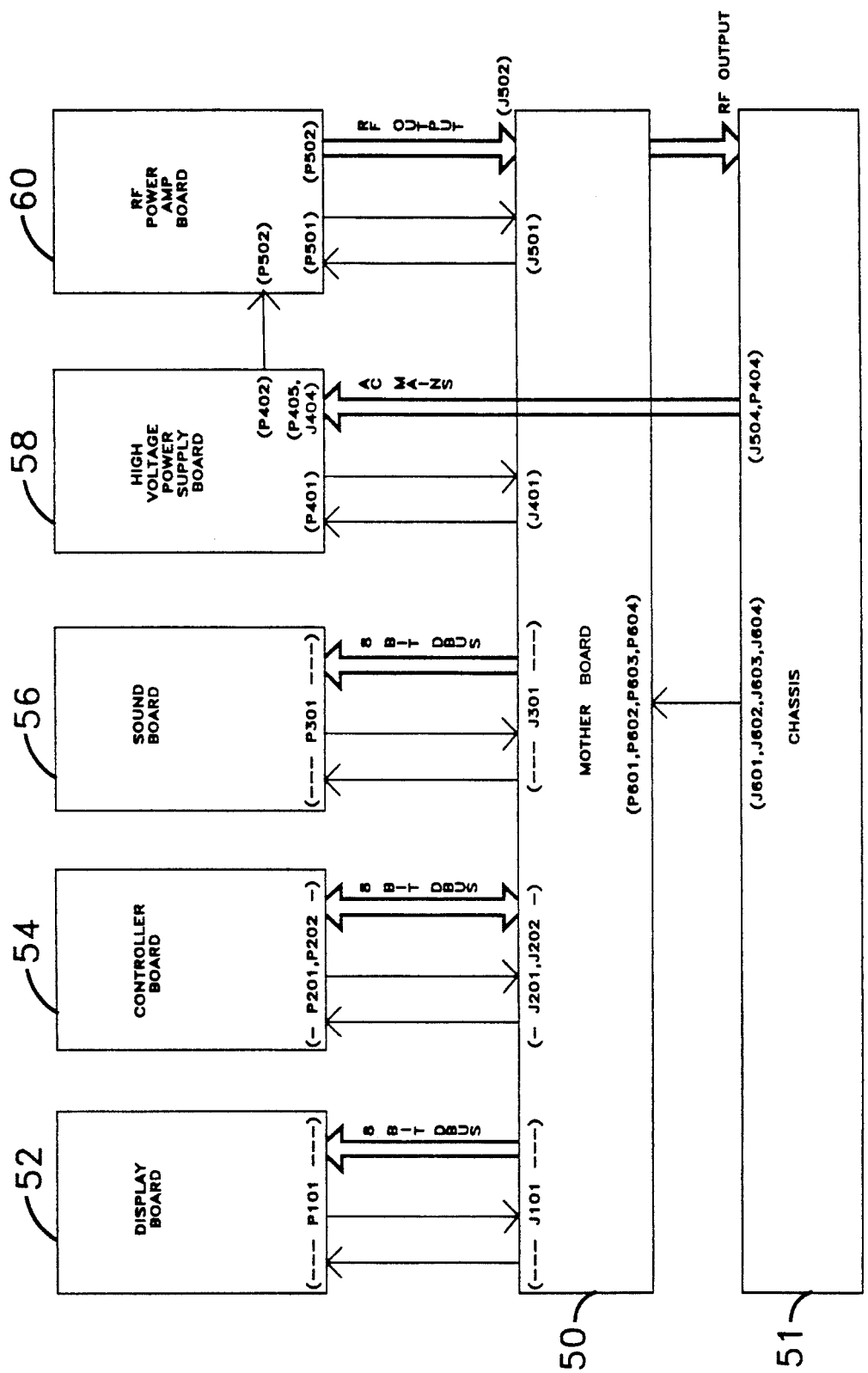
FIG. 2 is a general block diagram of the bipolar RF generator of FIG. 1.

Referring to FIG. 2, there is shown a general functional block diagram of the bipolar RF generator. The bipolar RF generator comprises a mother board printed circuit board 50 and five daughter printed circuit boards. The mother board 50, which is connected to a supporting chassis 51, includes a plurality of connectors (not shown) used for interconnecting the six printed circuit boards and acts as a common pathway for transmitting control signals and information between the various hardware devices located on the daughter boards. The connectors are conventional connectors which are well-known to those skilled in the art and will not be discussed further.

The first daughter board is a display board 52 which includes a plurality of LED displays and accompanying control circuitry. The second daughter board is a controller board 54 which includes an 8-bit microprocessor and a plurality of integrated circuits for providing input data or output data to the microprocessor. The third daughter board is a sound board 56 which includes the circuitry necessary for generating an audio voice response and tone information. The RF generator is capable of audibly indicating to the surgeon or other user certain information such as the power output level and the mode of operation. The fourth daughter board is a high voltage power supply board 58. The high voltage power supply board 58 includes an off-line switching-type power supply which utilizes the fly-back principle of voltage transfer and voltage isolation from the standard power line sources. The fifth daughter board is an RF power amplifier board 60 which generates an aperiodic coagulating waveform, or a cutting waveform at controllable power output levels.

DISPLAY BOARD

Figure 3:
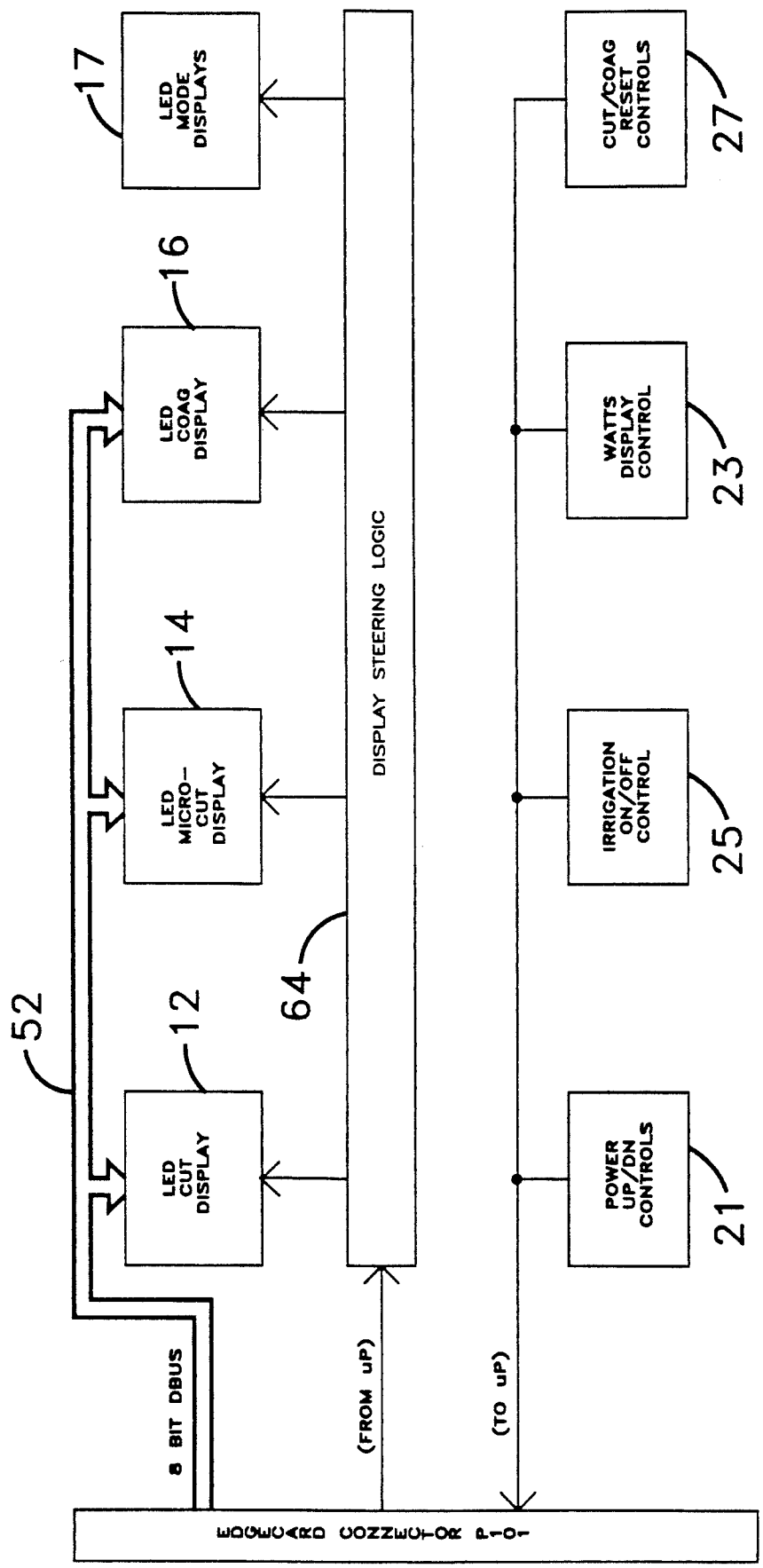
FIG. 3 is a general block diagram of a display printed circuit board of the bipolar RF generator of FIG. 1.

Referring specifically to FIG. 3, there is shown a schematic block diagram of the display board 52. The display board 52 comprises the circuitry for controlling and operating a plurality of LED displays described above. A first LED display 12 is an LED numeric display which indicates the power output setting of the RF generator when the RF generator is operating in the cut mode. The power output setting during operation in the cut mode is preferably between 20 W and 200 W and may be modified in increments of 20 watts. A second LED display 14 is an LED numeric display which indicates the power output setting of the RF generator when the generator is operating in the microcut mode. The microcut mode provides a lower power cutting setting and lower impedance than the cut mode. The range of power settings when operating in the microcut mode is preferably between 0.7 W and 17 W and is user adjustable. A third LED display 16 is a numeric LED display which indicates the power output setting of the RF generator when the generator is operating in the coagulation mode. The range of the power settings during operation in the coagulation mode is preferably between 0.7 W and 50 W and is user adjustable.

A fourth LED mode display 17 comprises a plurality of differently colored individual LEDs which when illuminated indicate the mode of operation of the RF generator. The modes of operation of the bipolar generator include, but are not limited to the cut mode, the microcut mode, the coag mode and an irrigation mode.

The display board 52 further includes circuitry for controlling a plurality of switches located on the front panel 10 of the RF generator which are manipulated by an operator to cause the RF generator to perform a desired operation. A first set of switches 21 controls the amount of output power generated by the RF generator. The switches can either increase or decrease the amount of power going to the bipolar pen 38. An irrigation switch 25 selectively activates a supplemental irrigation source which will be described in detail hereinafter. A watts display switch 23 controls and indicates when the power is being displayed in watts. A cut/coag reset switch 27 resets either the cut power level or the coagulation power level which has been adjusted during operation to a predetermined initial level.

Figure 5A:
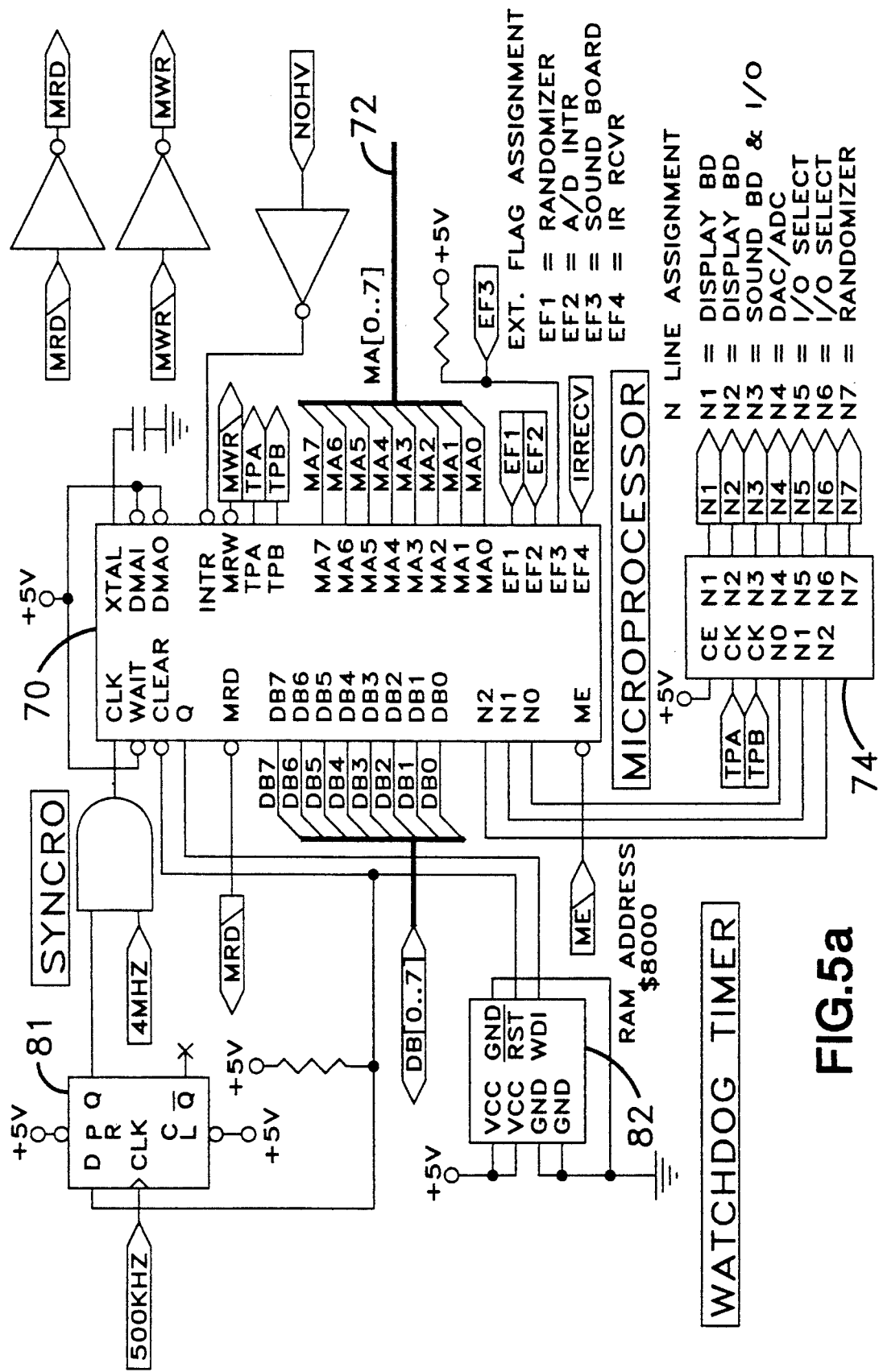
FIGS. 5a and 5b are a circuit schematic of a microprocessor and memory circuit of the controller board of FIG. 4.
Figure 5B:
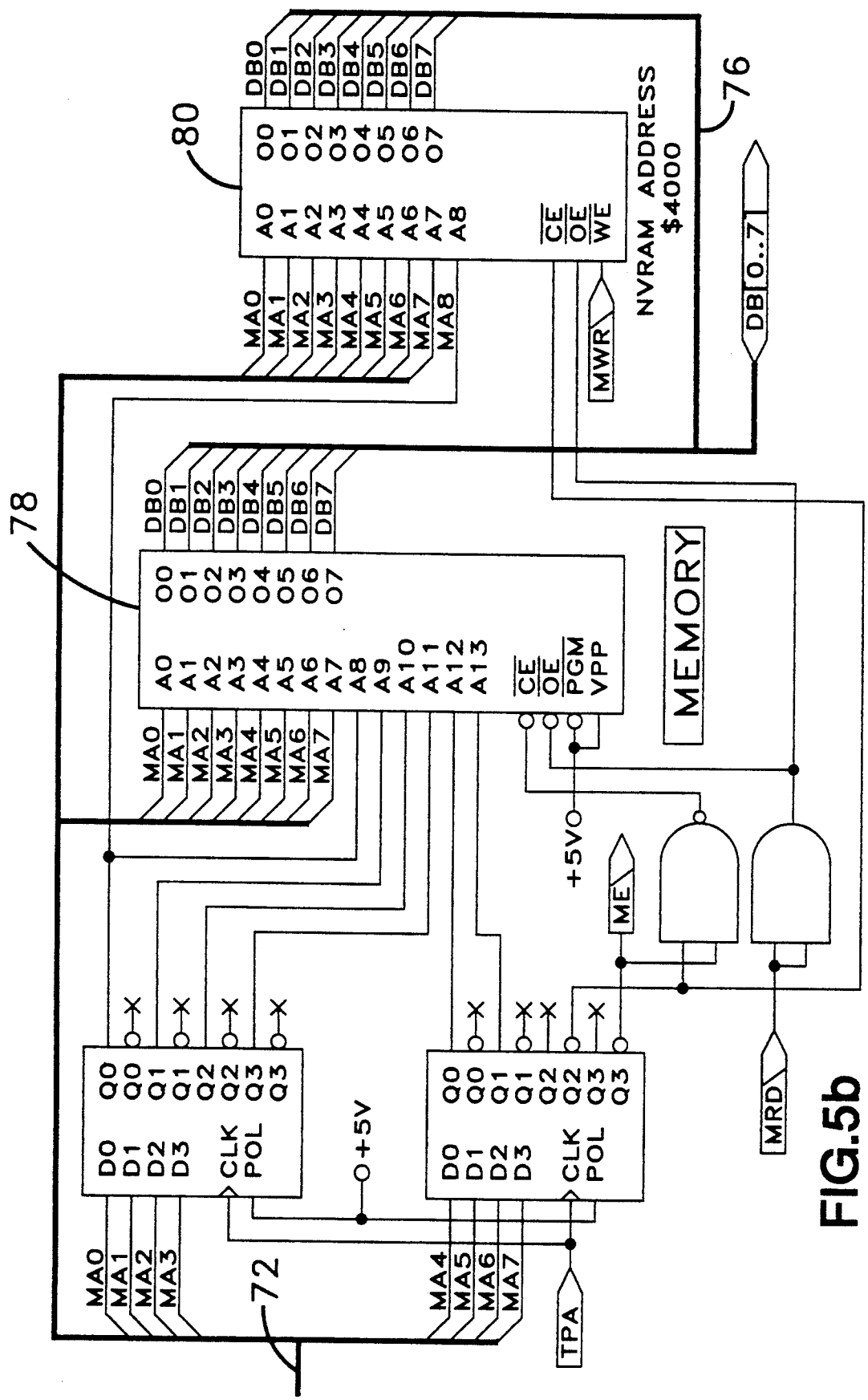

Each numeric LED display located on the display board 52 is controlled by steering logic 64. The steering logic 64 supplies control signals to a plurality of LED drivers (not shown) associated with the various LED displays. Each LED driver is associated with a single LED. The steering logic 64 also latches data from an eight-bit data bus associated with a microprocessor (FIGS. 5–6) which will be discussed in further detail hereinafter. The data from the microprocessor provides an indication of the power setting of the RF generator and watts/Malis units, irrigation, mute, microcut, cut, and coag selection modes.

An I/O decoder 74 (FIGS. 4–5) connected to the microprocessor provides two functions responsible for controlling the LED numeric displays. The first function output N1 selects the most significant bytes of the cut and coagulation numeric displays. The second function output N2 selects the two least significant bytes on the cut, microcut and coagulation displays. The LED numeric displays receive signals from the microprocessor indicating the current mode of operation of the generator. These signals include a foot pedal down signal FTPDON, a high power cut signal HPCUT, a low power cut signal LPCUT, a coag signal COAG, and a blink signal BLINK which causes a mode indicating a periodic signal to be produced during the cut and coagulation modes as will be discussed in detail hereinafter.

CONTROLLER BOARD

Figure 4:
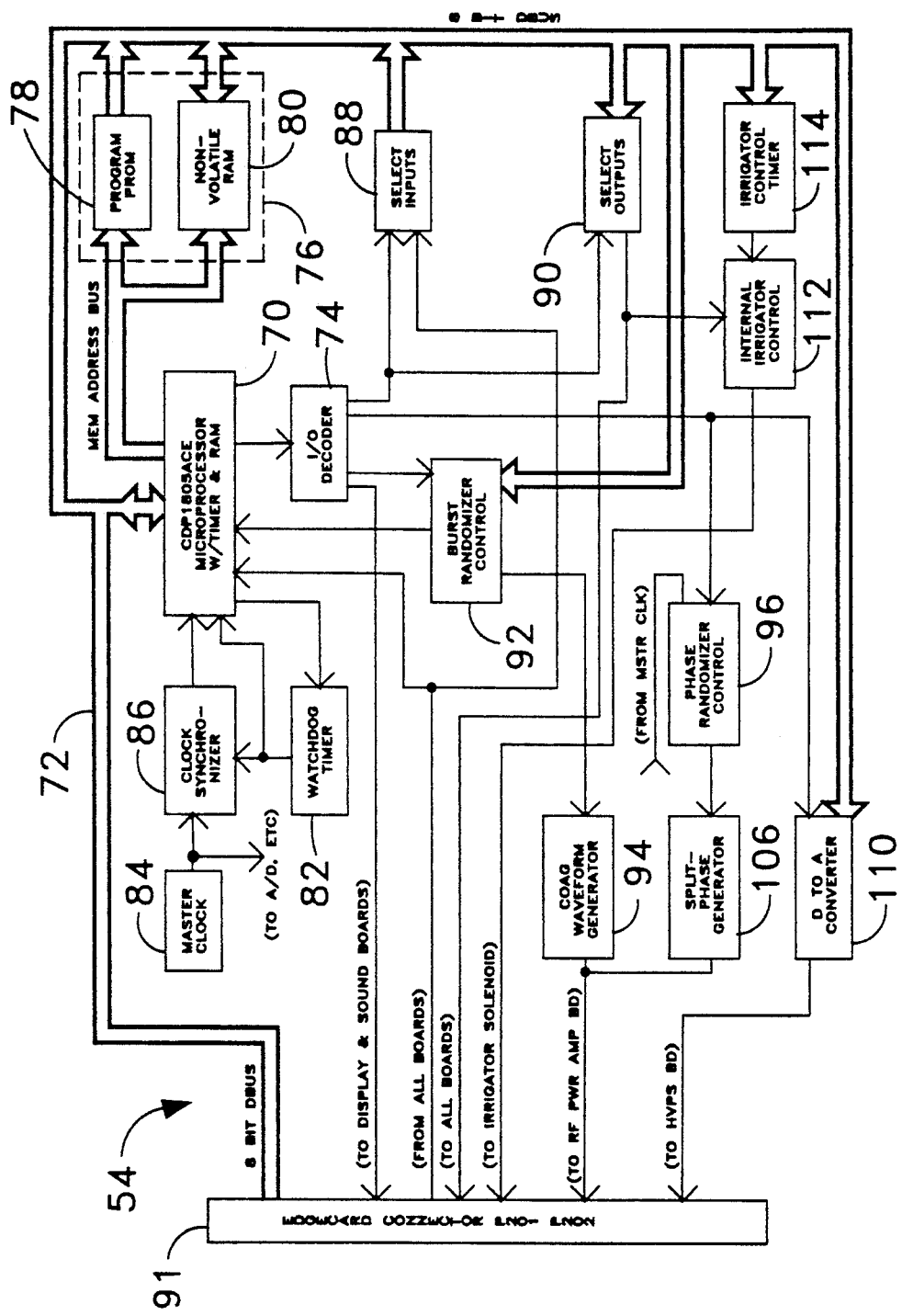
FIG. 4 is a general block diagram of a controller printed circuit board of the bipolar RF generator of FIG. 1.

Referring specifically to FIG. 4, there is shown a schematic diagram of the preferred embodiment of the controller board 54. The controller board 54 preferably includes an 8-bit microprocessor 70. In the preferred embodiment, the microprocessor 70 is an RCA/Harris 1805 microprocessor which includes timing and random access memory RAM. However, it is to be understood by those skilled in the art that any suitable processor or microprocessor can be used without departing the scope and spirit of the present invention. The microprocessor 70 is connected to an eight-bit bidirectional data bus 72 which is capable of sending data to and from the various components located within the RF generator. An I/O decoder 74 is connected to the microprocessor 70 for receiving and transmitting data from and to the microprocessor 70. The I/O decoder 74 is preferably an N-line decoder which can be used for selecting up to seven functions. The N1-N7 outputs of the I/O decoder 74 control the numeric displays 12, 14, 16, a speech synthesizer, a digital to analog converter 110, an I/O select, the signal transmitted to the RF power amplifier board and a burst randomizer control 92.

The microprocessor 70 is also connected to a multiplexed sixteen-bit memory addressing circuit 76 which provides up to 64 kilobytes of data. The memory circuit 76 comprises a sixteen kilobyte EPROM or PROM 78, a 0.5 kilobyte non-volatile RAM 80 and a 64-byte RAM (not shown).

A-watchdog timer 82 connected to the microprocessor 70 provides a reset pulse to the microprocessor 70 during power up and when no signal is detected by a watchdog input pin (not shown) within 1 to 2.5 seconds.

A master clock generator 84 which includes a stable 8 MHz crystal and two ripple dividers (not shown) is also associated with the microprocessor 70. The ripple dividers provide continual, phase coherent division of the 8 MHz clock signal to produce a plurality of clock signals ranging from 4 MHz to 0.25 Hz. Each succeeding clock signal is half of the preceding signal. The master clock generator 84 is connected to a clock synchronizer 86 which synchronizes the generated clock frequencies transmitted to the various electrical components associated with the microprocessor 70. The microprocessor 70 receives an incoming clock signal which is preferably 4 MHz. Once the clock signal is received, the microprocessor 70 internally divides the clock signal by 8. This can cause problems if the microprocessor clock divider asynchronously divides other clock signals received from the various components which can lead to missing pulses which can produce an alteration in the coagulation waveform formed during the coag mode.

A 500 KHz clock signal is supplied by the master clock generator 84 to the clock synchronizer 86 which is the equivalent of the internal clock frequency of the microprocessor 70. The clock synchronizer 86 comprises a flip-flop 81 (FIG. 5) with an output that only changes when a rising clock edge is received at the 500 KHz clock input. The watchdog timer 82 sends a clear signal to both the clock synchronizer 86 and the microprocessor 70 indicating that the rising edges of both the 4 MHz clock and the 500 KHz clock are aligned so that the microprocessor 70 runs synchronously with the master clock generator 84.

Data to be latched onto the data bus 72 are received by a select inputs circuit 88 which places the data onto the 8-bit data bus 72. Data to be latched off the data bus 72 are received by a select outputs circuit 90 for transmission to an external circuit, such as the sound circuitry or display circuitry via the card connector 91.

Figure 6:
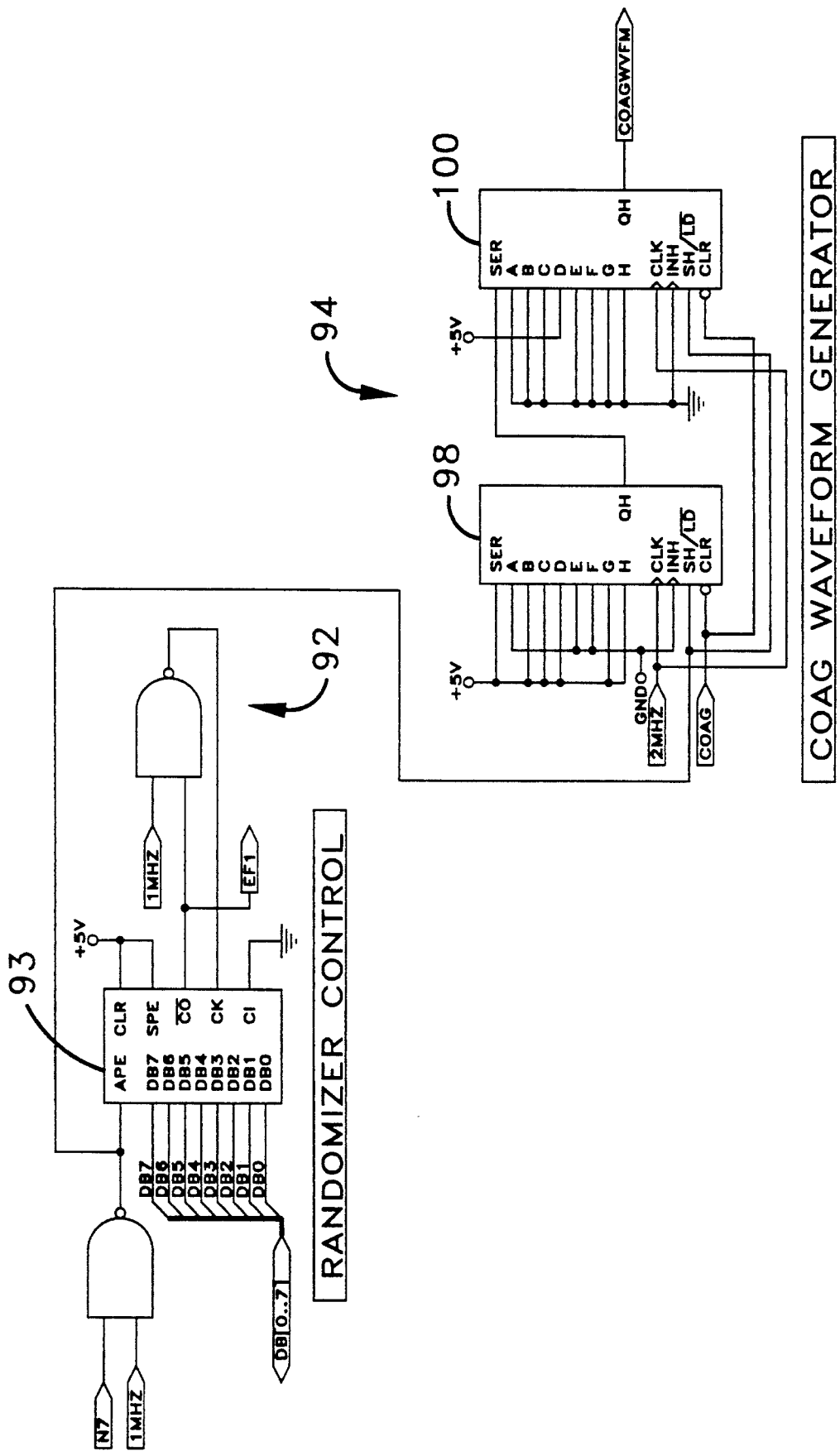
FIG. 6 is a circuit schematic of a burst randomizer circuit and a coagulation waveform generator of the controller board of FIG. 4.

Referring to FIGS. 4 and 6, a burst randomizer control circuit 92 is connected to the microprocessor 70 and provides additional delays which are not obtainable by the microprocessor 70 itself. -The burst randomizer 92 is activated by line assignment N7 of the I/O decoder 74. When N7 is asserted, data from the 8-bit data bus 72 are loaded onto an 8-bit binary down counter 93. The down counter 93 preferably clocks down at 1 MHz. However, it is to be understood by those skilled in the art that the down counter 93 can clock down at any desired speed. Each data byte latched into the counter 93 represents a delay in 1 microsecond increments. The data delay is used to control the start of the coagulation waveform bursts from the coagulation waveform generator 94 as will be described in detail hereinafter. When the down counter 93 is finished counting down by a given data byte, a signal is transmitted to the microprocessor 70 via an external flag line input EF1 which is used to provide the status of a given component.

A coagulation waveform generator 94 generates a power output waveform comprising groups of aperiodic sequences of damped bursts of high frequency (RF) signals. Each burst decays gradually from a controlled initial amplitude. The burst decay envelopes are uniform, that is, substantially identical from burst to burst. The interburst spacings are pseudo-random. The frequency of the RF signal within a burst is randomized by sweeping the frequency between preset limits.

Referring to FIGS. 4 and 6, the coagulation waveform generator 94 comprises two 8-bit shift registers 98, 100 which are connected together in series to form a 16-bit word. It is to be understood by those skilled in the art that a 16-bit shift register could be used without departing from the scope and spirit of the present invention. A clock signal transmitted to the coag waveform generator 94 may either be held at 1 MHz (cut mode) or varied between limits of 1 MHz plus or minus 4% (coag mode) as will be described hereinafter. Once the coag waveform generator 94 receives a burst or a start pulse from the burst randomizer 92, the shift registers 98, 100 provide a series of output pulses at a 0.5 microsecond rate. The burst randomizer 92 shifts the input load of the shift registers 98, 100 to produce pulses which are out of phase from one another at a 2 MHz rate. A divided down signal from the master clock (2 MHz) and associated with the shift registers 98, 100 produces a constant clock pulse of 0.5 microseconds. The 2 MHz clock causes the shift registers 98, 100 to have the following pulse waveform pattern when the burst randomizer 92 causes the shift registers 98, 100 to load: 2 microseconds on, 0.5 microseconds off; 1.5 microseconds on, 1 microsecond off; 1 microsecond on, 1.5 microseconds off; 0.5 microseconds on, 2 microseconds off. The total duration for the entire waveform is 10 microseconds. The coag waveform generated is shunted during the cut mode since an asynchronous signal is not required.

The pulse waveform generated by the shift registers 98, 100 is transmitted to a MOSFET (not shown). When a DC voltage enters the drain of the MOSFET, the pulse waveform is passed through a low pass filter which rounds out the edges of the waveform. The modified pulse waveform is transmitted to a bridge amplifier which will be described in detail hereinafter. The modulated waveform transmitted to the bridge amplifier forms a damped sinusoidal wave which is 10 microseconds in duration in accordance with the above-described pulse waveform pattern.

Figure 7:
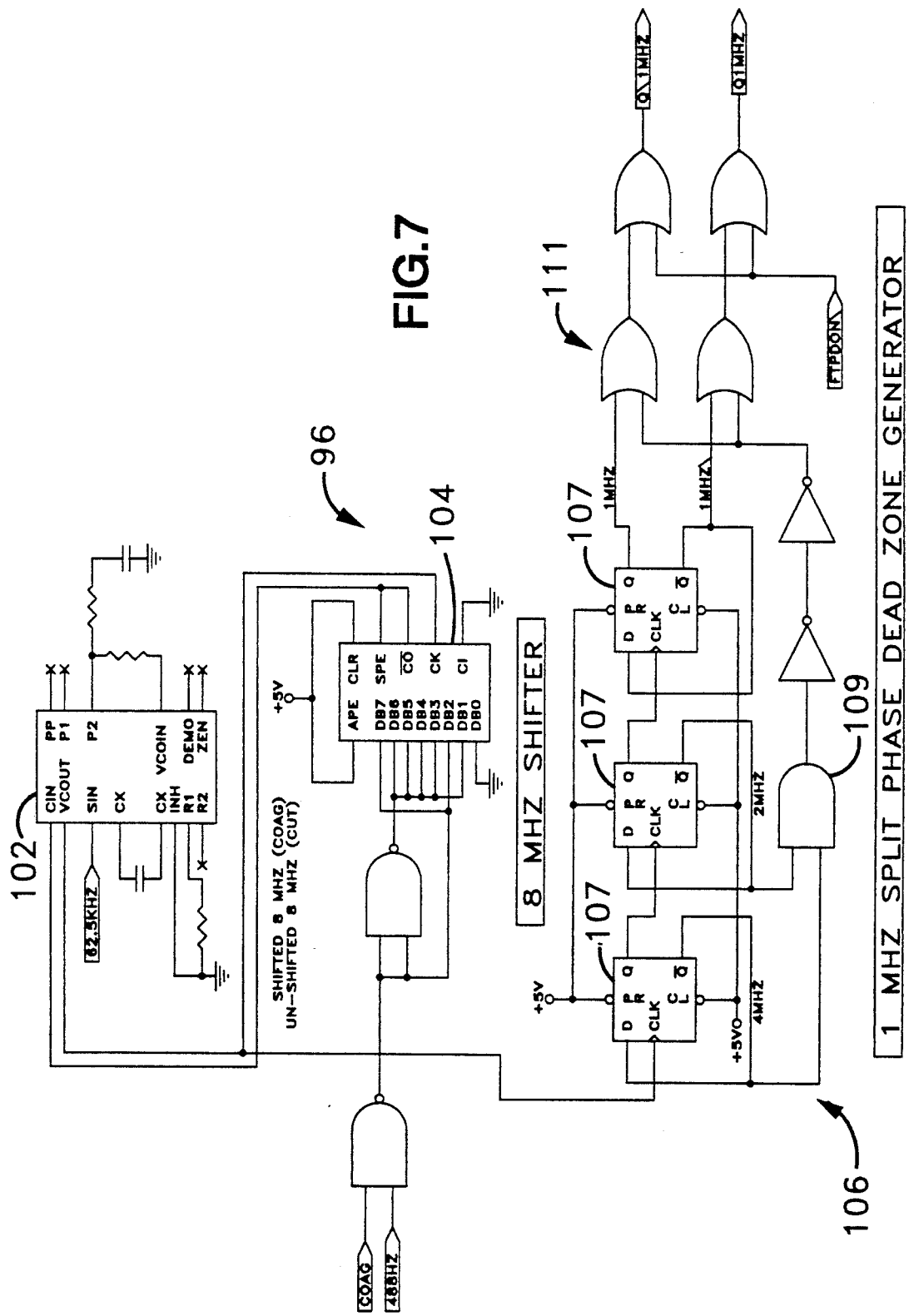
FIG. 7 is a circuit schematic of an 8 MHz shifter and 1 MHz split phase dead zone generator of the controller board of FIG. 4.

Referring to FIGS. 4 and 7, the frequency of the ramped pulses inside each burst is varied in the coagulation mode by an 8 MHz shifter which is also referred to as a phase randomizer control circuit 96. The 8 MHz shifter 96 is used to produce a base frequency of 1 MHz which can be shifted by plus or minus 4%. The base frequency is synthesized with a phase locked loop circuit 102 which has a voltage controlled oscillator output (VCO) of 8 MHz. The VCO output is divided by an 8-bit binary down counter 104 and is fed back to a reference input of the phase locked loop circuit 102. A second reference input to the phase locked loop circuit 102 is connected to a 62.5 KHz reference clock generated by the master clock generator 84. The 8-bit binary down counter 104 preferably divides the clock input at a ratio which provides a 62.5 KHz output. The 8-bit binary down counter 104 can also receive a 488 Hz reference clock signal which controls the rate at which the frequency of the VCO is swept. This causes the VCO output to be 8 MHz plus or minus 4% which is swept at a rate of change of 488 Hz. The varied 8 MHz signal is used to produce the asynchronous coagulation waveform.

The varied 8 MHz signal is transmitted from the 8 MHz shifter 96 to a 1 MHz split phase dead zone generator 106. As will be discussed hereinafter, an RF power bridge amplifier comprising field effect transistors requires a 1 MHz signal input. However, due to the turn off delay propagation nature of the field effect transistors, a shorter duty cycle is required to prevent both halves of the bridge amplifier from turning on at the same time thereby reducing efficiency. The duty cycle is preferably 37% on and 63% off. The 8 MHz outputs from the 8 MHz shifter 96 are sequentially divided by two through a series of flip-flops 107. The resulting outputs are two 1 MHz signals, wherein each 1 MHz signal is out of phase with the other 1 MHz signal by 180°. The 2 MHz output from one of the flip-flops and the 4 MHz output from a different flip-flop are combined at AND gate 109 to form a delay signal. The delay signal is combined through suitable logic gates 111 with the two 1 MHz signals to form two 37% duty cycle waveforms Q1MHz and Q/1MHz. The rising edge of each 1 MHz waveform is shifted 180° with respect to the other to provide for proper RF bridge amplifier operation.

Referring to FIG. 4, a digital to analog converter (DAC) 110 receives digital signals from the 8-bit data bus 72, and converts the digital signals to analog waveform information which is used by the high voltage power supply which will be described in detail hereinafter. Eight bits of hexadecimal data or 256 bits of decimal data are applied to the DAC 110. The data are loaded onto the DAC 110 when both the N4 signal from the I/O decoder 74 and a MRD signal (FIG. 5) from the microprocessor 70 are present at the DAC input.

An internal irrigation control 112 is used to control the amount of irrigation fluid transmitted to the bipolar pen 38 and the flow rate. An irrigator control timer 114 acts in conjunction with the internal irrigator control 112 to determine when the irrigator is to be switched on and off. The use of the irrigation and the amount of irrigation is determined by the irrigation on/off control 25 located on the display board 52.

SOUND BOARD

Figure 8:
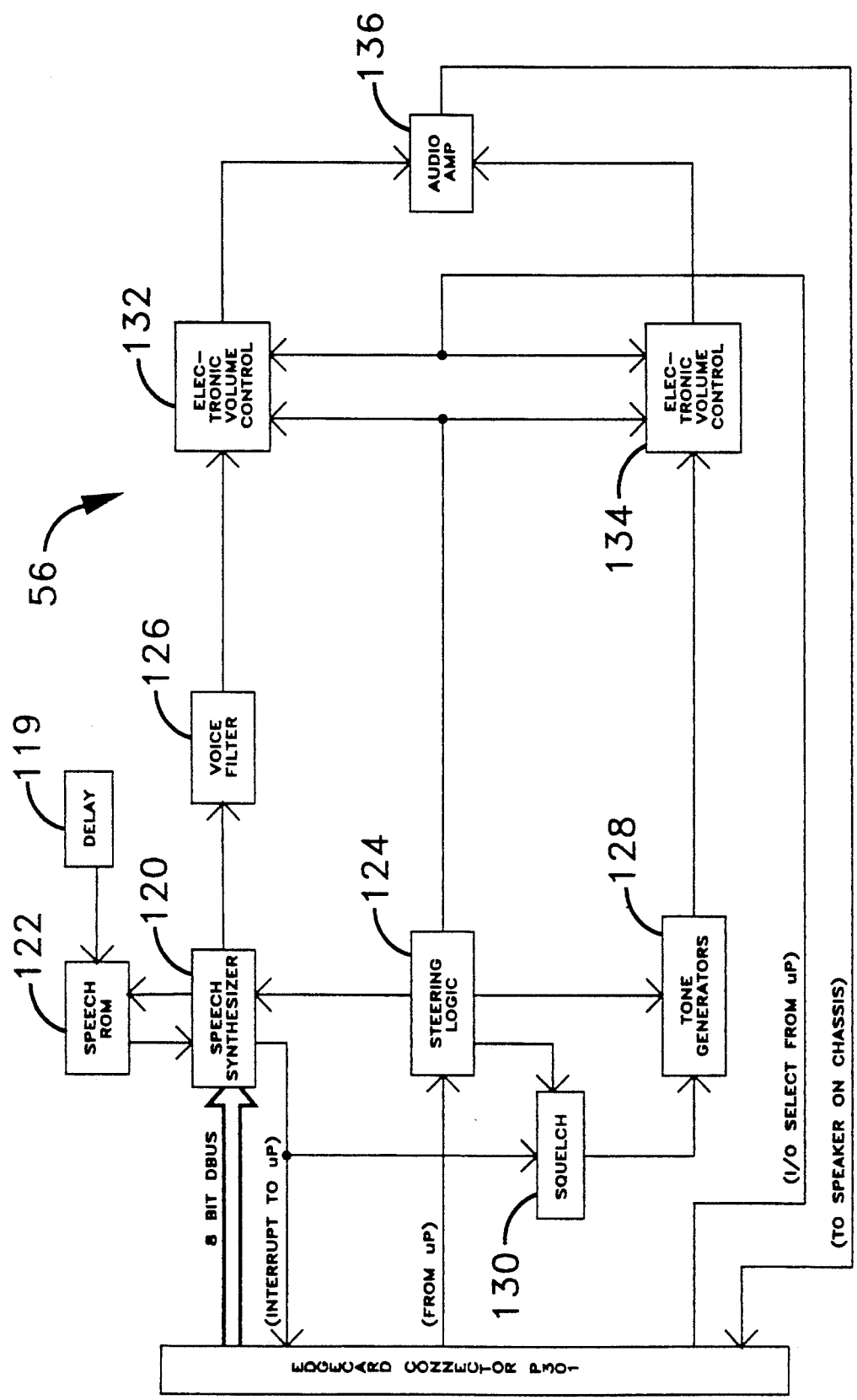
FIG. 8 is a general block diagram of a sound printed circuit board of the bipolar RF generator of FIG. 1.

Referring to FIG. 8, the sound board 56 provides all audio outputs from the RF generator. In response to the cut or coag mode signals, the microprocessor 70 controls a speech synthesizer processor 120 which provides voice information for communicating predetermined stored audio messages to the operator regarding the status of the RF generator and its features. The speech synthesizer processor 120 also sounds a minor or major chord (tones) depending on the mode of operation of the RF generator. In the preferred embodiment a major chord is continuously sounded when operating in the coag mode and a minor chord is continuously sounded when operating in the cut mode. Voice messages can be produced (from storage) to indicate a power setting, a malfunction of the burst randomizer, loss of power output or simultaneous depression of the foot pedals. Once the malfunction or other condition is corrected, the speech synthesizer processor 120 resumes normal operation.

The speech synthesizer processor 120 preferably is a Digitalker manufactured by National Semiconductor and is connected to a speech ROM or EPROM 122 for storing voice information used to produce the audio messages. It is to be understood by those skilled in the art that any speech synthesizer can be used without departing from the scope and spirit of the present invention. The speech synthesizer processor 120 is activated by a combination of signals sent from the microprocessor 70, the I/O decoder 74 (N3) and the 8-bit data bus 72. When the speech synthesizer processor 120 simultaneously receives a write pulse from the N3 signal of the I/O decoder 74 and data from the 8-bit data bus 72, the speech synthesizer 120 is activated. The data transmitted from the microprocessor 70 to the speech synthesizer 120 determines which word or words are to be selected from the voice information contained within the speech EPROM 122.

Steering logic 124 is used to identify when the required signals are received by the speech synthesizer processor 120 and to retrieve the selected word or words from the EPROM 122. The selected word or words are transmitted through a voice filter 126.

The sound board 56 also comprises a plurality of tone generators 128 which are preferably square wave generators capable of operating at three different audio frequencies. In the preferred embodiment, a single tone of 390 Hz is shared by both the cut and coag modes. A NAND gate determines which of the two tones are to be used. In the event that there is no foot pedal activity or the speech synthesizer 120 is accessed, the tones are squelched by a squelch circuit 130.

Two electronic volume control circuits 132, 134 are provided to control tone volume and voice volume, respectively. The volume control circuits 132, 134 are similar to digital to analog converters and comprise 100 internal steps which are used to control the degree of volume transmitted from the sound board 56. Both the tone volume and the voice volume can be controlled to either be increased or decreased in magnitude. Once the voice volume and tone volume signals are adjusted to the desired volume, the audio information is transmitted to an audio amplifier 136 which amplifies the audio signals and transmits the amplified signals to a speaker (not shown) located on the chassis 51. In addition, a delay signal may be provided by a delay circuit 119 to cause a small time delay during power up to suppress noise generated from the speech synthesizer 120 and the tone generators 128.

HIGH VOLTAGE POWER SUPPLY BOARD

Figure 9:
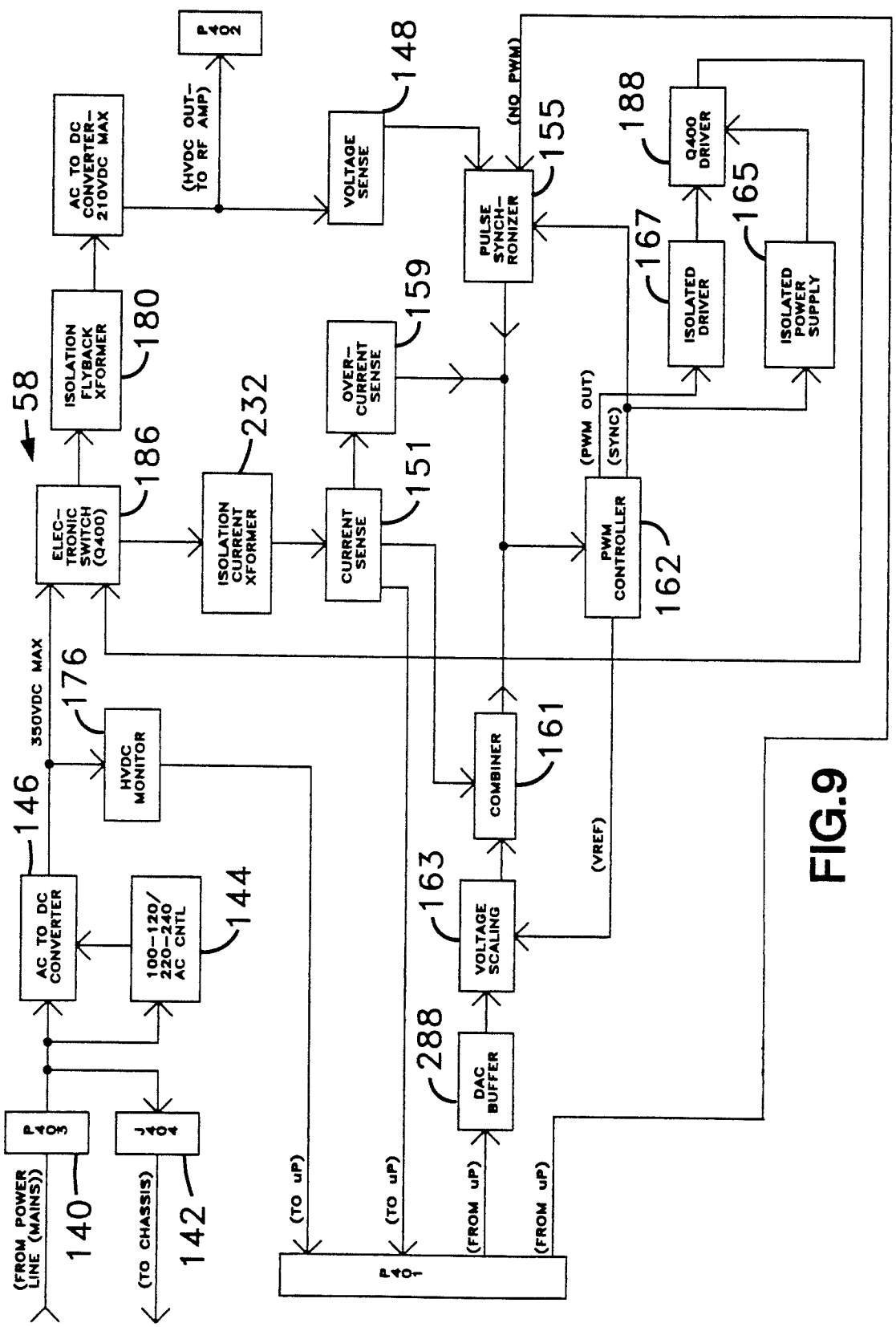
FIG. 9 is a general block diagram of a high voltage power supply printed circuit board of the bipolar RF generator of FIG. 1.

Referring to FIG. 9, there is shown a general block diagram depicting the high voltage power supply board 58 in accordance with the present invention. The high voltage power supply is preferably an off-line switching type power supply which utilizes the flyback principle of voltage transfer and isolation from standard power line sources. In the preferred embodiment, the power line sources include a connector 140 for connecting to either a 110/120 VAC or a 220/240 VAC connection. An AC control circuit 144 determines which power source is being utilized by the power supply board 58. Once the desired power source is determined, the voltage received by the power supply board 58 is converted to a DC voltage by an AC to DC converter 146. A second connector 142 is employed for providing AC power from connector 140 to the chassis 51 for powering the other boards.

An HVDC monitor 176, which in the preferred embodiment is an optoisolator (FIG. 10a), monitors the DC voltage from the AC to DC converter 146 and detects when a loss of high voltage occurs. The HVDC monitor 176 transmits the detection of a loss of high voltage to the microprocessor 70 located on the controller board 154 (FIG. 4) for alerting the user.

An electronic switch 186, which is preferably a MOSFET, also receives the DC voltage from the AC to DC converter 146. When the electronic switch 186 is in the ON position, the DC voltage is transmitted to an isolation flyback transformer 180. The electronic switch 186 primarily receives a control voltage from a pulse width modulator (PWM) controller 162, which is preferably a chip, in the form of a PWM signal. The PWM signal is driven by an FET driver circuit 188 which, in combination with an isolated driver 167, buffers the PWM signal from the PWM controller 162 to the electronic switch 186. However, the PWM signal is not always present. When the PWM signal pulses are absent from the PWM controller 162 circuit, an isolated power supply 165 supplies a steady voltage to the electronic switch 186. The isolated power supply 165 provides a 15 V volt supply signal to the electronic switch 186 through the FET driver circuit 188.

The isolation flyback transformer 180 receives and stores the voltage from the electronic switch 186 in its primary winding as long as the electronic switch 186 is ON. The current contained within the primary winding of the flyback transformer 180 ramps linearly upwardly while the electronic switch 186 is conducting (ON). During this time, the current contained within the primary winding of the flyback transformer 180 is essentially trapped and no current is received by the secondary winding of the flyback transformer 180. When the electronic switch 186 is in the OFF position (not conducting the HVDC), the trapped current from the primary winding of the flyback transformer 180 transfers to the secondary transformer winding which in turn transmits the voltage to a voltage sensing circuit 148. The voltage sensing circuit 148 is preferably a comparator which compares the received voltage from the transformer secondary winding with a reference voltage received from the DAC 110 (FIG. 4) located on the controller board 54. The reference voltage received from the DAC 110 determines the desired output voltage from the power supply. If the DC voltage from the transformer secondary winding is greater or less than the DAC reference voltage by a predetermined amount, the DC voltage from the transformer secondary winding is adjusted by the PWM controller 162 to be within the range of the desired output voltage for the power supply board 58 as determined by the DAC reference voltage.

The DAC reference voltage is received by the power supply board 58 and buffered by a DAC buffer 288. The buffered DAC voltage is received by a voltage scaling circuit 163 which preferably includes a clamping amplifier 286 (FIG. 10b) which clamps or scales the DAC voltage to approximately 1.9 V for DAC reference voltages which exceed 3.0 V. The voltage scaling circuit 163 thus limits the amount of energy that can be delivered to the secondary winding of the flyback transformer 180. By clamping the DAC reference voltage, excessive overshoot during periods of light or no loads is prevented.

A combiner circuit 161 monitors the peak current of the primary winding of the flyback transformer 180 from a current sensing circuit 151 and compares the peak primary current to a reference current derived from the DAC voltage. If the peak primary current exceeds the reference current, a comparator 150 (FIG. 10b) located within the combiner circuit 161 goes high and causes the PWM controller 162 to shut down. The combiner circuit 161 prevents the current of the primary winding of the flyback transformer 180 from attaining values which would result in saturation of the primary winding of the flyback transformer 180.

A number of protection circuits are associated with the power supply 58 in order to prevent an overshoot condition. A current sensing circuit 151 determines the peak current of the primary winding of the flyback transformer 180 which is controlled by the DAC reference voltage signal. The current sensing circuit 151 operates on a cycle by cycle basis and controls the pulse width of the DC voltage signal from the flyback transformer secondary winding as modulated by a pulse synchronizer 155.

A second protection circuit is an overcurrent sensing circuit 159. The overcurrent sensing circuit 159 detects when the peak primary current overshoots the desired value and causes the pulse width modulation (PWM) controller 162 to shutdown.

Referring to FIGS. 10a–10e, there is shown a series of detailed schematics depicting portions of the circuitry of the high voltage power supply board 58 of FIG. 9. The power supply board 58 provides to the RF generator a variable DC output voltage which is controlled by a reference voltage derived from the digital-to-analog converter (DAC) 110 located on the controller board 54 (FIG. 4). Voltage control is derived from a high-speed comparator 150 (FIG. 10b) which compares the desired DC output voltage from the power supply board 58 to the DAC reference voltage. A change in the DAC reference voltage causes a proportional change in the desired DC output voltage from the power supply.

BIAS SUPPLY

Referring to FIG. 10e, the power supply control circuitry provides +15 V and −15 V regulated bias voltages and acts as an isolated power supply 165 to the electronic switch 186. The input voltages to the power supply control circuitry are raw +18 V and −18 V voltage supply inputs available at the board connector to the mother board 50. Standard three-terminal voltage regulators 152, 154 are used to provide the regulated +15 and −15 bias voltages. A pair of LC circuits 156, 158 provide filtering for the raw +18 V and −18 V input voltage and ensure that radio frequency noise is not injected into the control circuitry through the bias voltage supply. A plurality of capacitors 160a, 160b, 160c, 160d, 160e serves as output filters for the three-terminal voltage regulators 152, 154. Typically, the load on the −15 V bias voltage supply is nominally less than 10 ma. The +15 V bias voltage supply provides bias power to the pulse width modulation (PWM) controller 162 as well as analog processing electronics. The load current from the +15 V bias power supply can vary from 75 ma to 200 ma depending upon the mode of operation of the RF generator.

POWER PATH

Figure 10A:
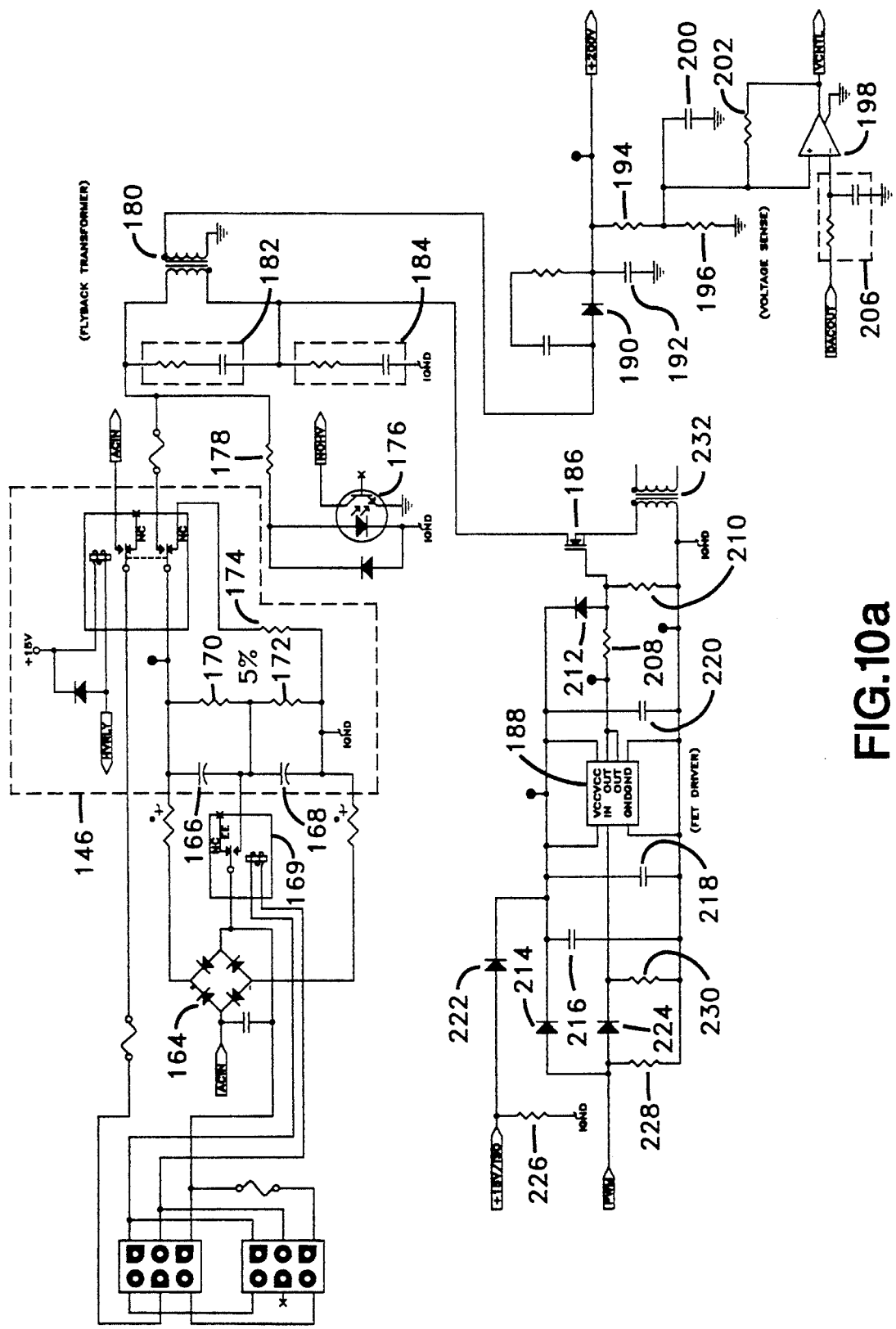

Referring to FIG. 10a, input power is derived from the AC main via bridge diodes 164 and a pair of filter capacitors 166, 168 which operate as a voltage doubler system when relay 169 is in the 120 V AC mode. The power supply can also operates in a 220/240 V AC mode when the relay 169 is de-activated. Associated with the filter capacitors 166, 168 are voltage balancing resistors 170, 172 which make sure that any received voltage is divided equally between the capacitors 166, 168. A bleeder resistor 174 provides a bleed path for the filter capacitors 166, 168 to accelerate discharge when the RF generator is removed from the power source. In the preferred embodiment, the effective time constant for the capacitor discharge is approximately 16 seconds.

An optoisolator 176 indicates to the microprocessor 70 (FIG. 4) the occurrence of a loss of high voltage in the power supply. High voltage losses typically occur when a fuse has been blown to create an open circuit. A resistor 178 provides bias current to the optoisolator 176. An AC to DC converter 146 (FIG. 9) converts the AC bias voltage to a DC voltage signal. The DC voltage signal is presented to the primary winding of a flyback transformer 180. In the preferred embodiment, the flyback transformer 180 has primary and secondary inductances of generally equal value which are approximately 165 microhenries. However, it is to be understood by those skilled in the art that the inductance of the flyback transformer 180 can be any appropriate value without departing from the scope and spirit of the present invention. A pair of snubber circuits 182, 184 are associated with a power FET or electronic switch 186 and the flyback transformer 180. Leakage inductance in the flyback transformer 180 causes energy to be stored in the primary winding during the ON time of the power FET 186. The energy from the primary winding of the flyback transformer 180 is not transferred to the secondary winding of the flyback transformer 180 during the ON time of the power FET 186. The energy stored within the primary winding is considered to be trapped and causes the voltage at the drain of the power FET 186 to rise abruptly when the power FET 186 turns OFF. The FET drain voltage continues to rise until a path is found for the energy stored in the leakage inductance. In the preferred embodiment, the path is formed by the pair of snubber circuits 182, 184.

The primary winding of the flyback transformer 180 is switched ON and OFF by the power FET 186. Drive signals transmitted to an FET driver circuit 188, which buffers a PWM drive signal originating from the PWM controller 162 (FIG. 9) to the FET 186 causing the power FET 186 to begin conducting. A current in the primary winding of the flyback transformer 180 ramps linearly upwardly while the power FET 186 is conducting. At the same time, the secondary winding of the flyback transformer 180 is negative and reverse biases a diode 190 causing the current passing through the diode 190 to be zero.

A load current is supplied by a capacitor 192 when the power FET 186 is conducting. When the power FET 186 turns OFF, the current in the primary winding of the flyback transformer 180 decreases rapidly to zero and the current is transferred to the secondary winding of the flyback transformer 180. The current received from the primary winding of the flyback transformer 180 causes the secondary winding of the flyback transformer 180 to become positive and forward biases the diode 190. The voltage of the secondary winding of the flyback transformer 180 rises until it is equal to the voltage of the capacitor 192. The current of the secondary winding of the flyback transformer 180 initially reaches a value approximately equal to the peak current of the primary winding of the flyback transformer 180, then decays linearly. The current of the secondary winding of the flyback transformer 180 may or may not decay to zero. The average value of the current of the secondary winding of the flyback transformer 180 as calculated over a full cycle is equal to the load current of the capacitor 192.

Figure 10B:
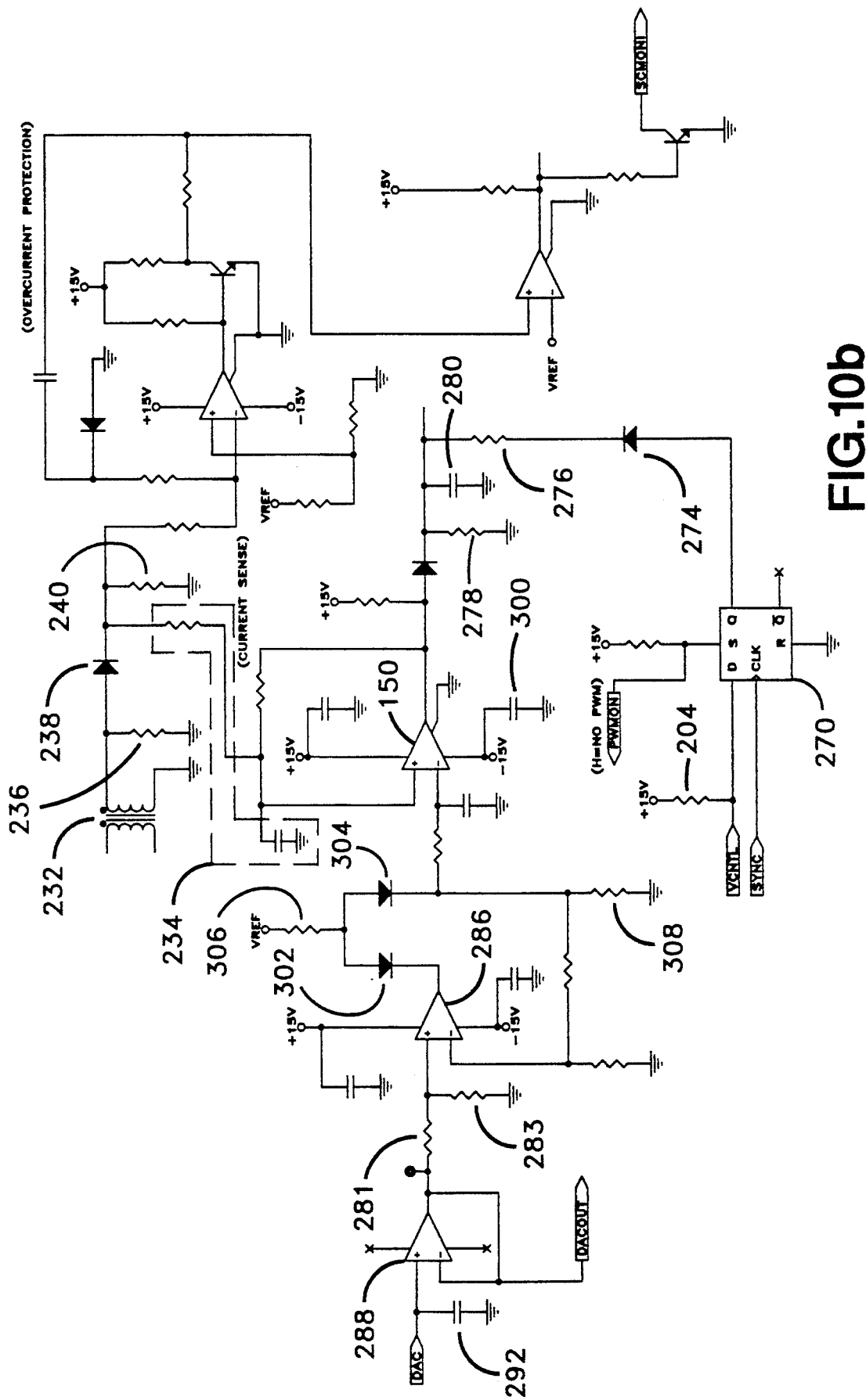

The desired output voltage of the power supply is sensed by a pair of voltage divider resistors 194, 196. The voltage divider ratio is nominally 1/46.2. A voltage produced by the voltage divider 194, 196 is transmitted to a comparator 198 where it is compared to the DAC reference voltage from the microprocessor 70. A comparator output signal VCNTL is either high or low depending on the result of the comparison. The output signal VCNTRL is presented to control electronics as will be discussed in detail hereinafter. A second capacitor 200 provides noise filtering at the input to the comparator 198 and a resistor 202 provides hysteresis to ensure stable transitions at the output of comparator 198. The comparator 198 has an open collector output which is pulled up to +15 V by a resistor 204 (FIG. 10b). An RC circuit 206 provide low pass filtering for the DAC reference voltage.

FET DRIVE CIRCUIT

The FET drive circuit 188 provides rapid turn-on and turn-off drive signals to the power FET 186. A series resistor 208 precludes oscillation at the gate of the power FET 186. The FET drive circuit 188 is capable of sourcing and sinking the high peak currents of the primary winding of the flyback transformer 180 required to overcome the Miller effect which is associated with the power FET 186. A resistor 210 provides a leakage current path from the gate of the FET 186 to the source of the FET 186 in the event of a failure in the FET drive circuit 188. The resistor 210 serves no active purpose when the FET drive circuit 188 is operating properly.

A diode 212 clamps the gate source voltage of the power FET 186 to less than 20 V during transient conditions. The transformer secondary windings 266 (FIG. 10*d*) and 284 (FIG. 10*c*) are connected to the FET drive circuit 188. The secondary winding of the PWM transformer 284 carries the turn-on and turn-off signal (PWM signal) to control the power FET 186. The PWM signal is presented to the FET drive circuit 188 for buffering. The supply voltage for the FET drive circuit 188 is derived from the PWM signal via a diode 214 and a plurality of capacitors 216, 218, 220. The PWM signal is not always present at the power FET 186. An isolated +15 V secondary winding of the forward transformer 266 (FIG. 10*d*) provides power to the FET drive circuit 188 to ensure that the supply voltage remains at an appropriate level when the PWM signal is absent. A plurality of diodes 214, 222, 224 couple the PWM signals and the +15 V signals to the FET drive circuit 188 and act to isolate the signal sources from one another. A plurality of resistors 226, 228, 230 provide damping for the pulse transformer secondary windings to prevent ringing.

CURRENT SENSE CIRCUIT

Referring to FIGS. 10*a* and 10*b*, current through the power FET 186 is sensed via a current transformer 232. The output of the current transformer 232 operates as a current source while the power FET 186 is conducting. During the FET conduction time, the current of the primary winding of the current transformer 232 is scaled by the turns ratio (1:50) of the current transformer 232 and presented to a sense resistor 240 (FIG. 10*b*). The effective scale factor of the signal on the sense resistor 240 is preferably 2.78 A/V. The current signal is filtered by an RC circuit 234 before it is presented to a current control comparator 150. A current transformer core reset is provided by a resistor 236. While the power FET 186 is conducting, the secondary winding of the current transformer 232 forces current through a diode 238 and the sense resistor 240 causes a voltage drop across the diode and sense resistor 240. The voltage drop is also present across the current transformer 232 secondary winding during this time. The net result is a magnetizing current in the current transformer 232 which is opposite in direction to the current sense signal. The magnetizing current continues to build during the conduction time of the power FET 186. When the power FET 186 turns OFF, the secondary winding of the current transformer 232 behaves as an inductor with stored energy. The secondary winding of transformer 232 thus assumes a voltage required to maintain the present current level, which is the magnetizing current level.

PWM CONTROLLER CHIP

Figure 10C:
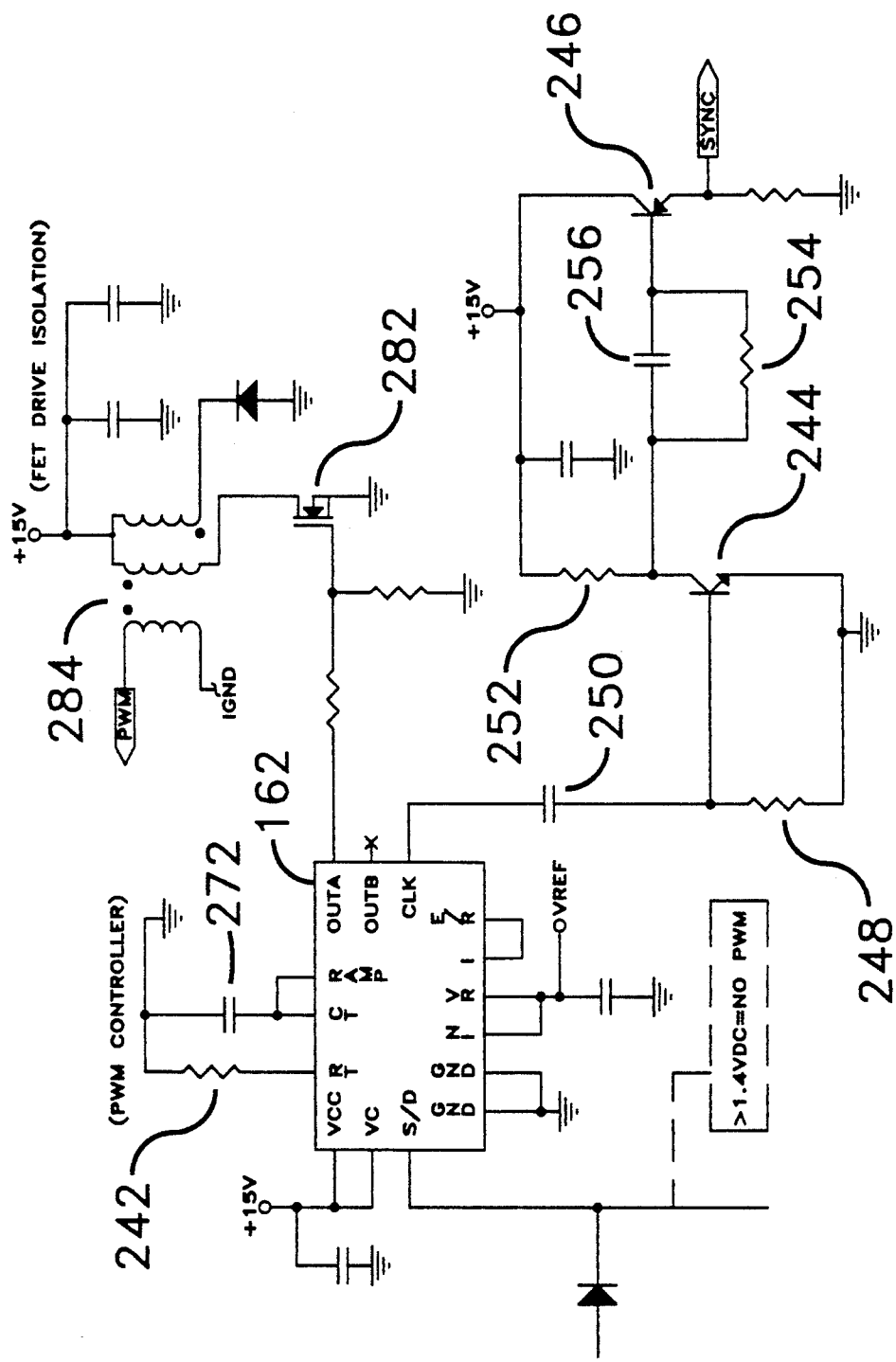

Referring to FIG. 10*c*, the PWM controller chip 162 contains all of the hardware required to implement the flyback topology of the power supply. A resistor 242 and capacitor 272 sets the internal oscillator frequency and dead time of the PWM chip 162. The resistor 242 sets the value of an internal current source used to linearly . charge the capacitor 272. The voltage on the capacitor 272 comprises a 1 V offset and a 1.8 V ramp which is monitored by an internal comparator within the PWM controller 162. When the ramp voltage of the capacitor 272 reaches an appropriate level, which in the preferred embodiment is approximately 3.5 V, the internal comparator turns on a transistor which discharges the voltage on the capacitor 272 and turns off the PWM chip 162 outputs. The time required for the capacitor 272 to discharge is identified as the dead time. During the dead time, the clock signal output CLK of the PWM chip 162 is high. In the preferred embodiment, the clock signal output CLK is approximately 2.2 V in amplitude with a 2.3 V DC offset. The value of the capacitor 272 controls the amount of dead time. In the preferred embodiment, an internal oscillator is set for 250 KHz with a dead time of approximately 0.3 microseconds. This results in a 125 KHz signal transmitted from output A of the PWM chip 162. The PWM chip 162 also includes a 5.1 V reference voltage, two output drivers and circuitry for shutting down the RF generator. A shutdown pin S/D provides duty cycle control as well as a means for preempting or interrupting an output pulse.

CONTROL AND INTERFACE

Referring to FIG. 10*c*, the clock output CLK of the PWM chip 162 is buffered and level shifted by a pair of transistors 244, 246. A first transistor 244 level shifts the clock output CLK from 4.5 V/2.3 V to 15 V/0 V. A resistor 248 and a capacitor 250 AC couple the clock output signal CLK from the PWM chip 162 to the first transistor 244. A resistor 252 provides a load to the collector of the transistor 244. This causes the signal present at the collector of the transistor 244 to be an inverted level shifted clock signal. A second inversion of the clock signal is accomplished by the second transistor 246. The collector signal of the first transistor 244 is applied to the base of the second transistor 246 through a resistor 254. A capacitor 256 is placed in parallel with the resistor 254 to provide overdrive to the second transistor 246 for rapid signal rise time. A SYNC signal is derived at the collector of the second transistor 246. In the preferred embodiment, the collector load to the second transistor 246 is relatively low which improves fall times by helping to sweep out the base charge of the second transistor 246. In the preferred embodiment, the collector load is approximately 330 ohms. The rising edge of the SYNC signal is critical with respect to rise time. In the preferred embodiment, the rising edge of the SYNC signal should be less than 75 ns.

As shown in FIG. 10*d*, the SYNC signal from the collector of transistor 246 is buffered by an FET driver 258 and is then applied to the gate of a MOSFET 260. A series resistor 262 prevents gate oscillations of the SYNC pulse. A second resistor 264 provides a path for leakage current in the event that the FET driver 258 fails due to a high impedance output. The MOSFET 260 drives the primary winding of a forward transformer 266 which generates the isolated +15 V signal used by the FET drive circuit 188 (FIG. 10*a*). The forward transformer 266 provides supply voltage power to the FET drive circuit 188 during periods when the normal PWM signal is not present. In the preferred embodiment, the forward transformer 266 is run at duty cycles of less than 50%. The forward transformer core resets itself through a winding which parallels the primary winding of the forward transformer 266 but which is 180° out of phase with the primary winding. As the MOSFET 260 is conducting, diode 268 is reversed biased. Diode 268 clamps the primary winding to +15 V during the MOSFET 260 off time. As MOSFET 260 is conducting, a magnetizing current stored within the forward transformer core is returned to the supply voltage. The voltage at the drain of the MOSFET 260 swings to +30 V when the MOSFET 260 shuts off. The drain voltage remains constant until a reset occurs from which it gradually decays to +15 V where it remains until the next cycle begins.

The SYNC signal is also used to synchronize a voltage control flip/flop 270 shown on FIG. 10b. The output signal VCNTRL of the voltage comparator 198 (FIG. 10a) is presented to the synchronizing flip/flop 270 where it is synchronized with the PWM chip oscillator by the SYNC signal before being presented to the shutdown pin (S/D) of the PWM chip 162. The synchronization is implemented to preclude sporadic duty cycle pulses from occurring which arise from the action of the shutdown pin. The synchronization causes an oscillator timing capacitor 272 (FIG. 10c) to discharge thereby shutting off the PWM chip outputs. In the event that the oscillator timing capacitor 272 begins to charge again, a shift in the oscillator frequency occurs. The synchronized VCNTL signal is applied to the shutdown pin of the PWM chip 162 via a diode 274 and resistor 276 arrangement. A second resistor 278 provides scaling to reduce the 15 V flip/flop output to less than 5 V and a capacitor 280 provides high frequency filtering. The diode 274 is required to isolate the voltage control flip/flop 270 from the shutdown pin when it is in a low state.

The PWM signal of the PWM chip 162 is buffered by a transistor 282 (FIG. 10c) and transformer 284 (FIG. 10c) coupled to the FET drive circuit 188. In the preferred embodiment, the PWM signal is approximately 125 KHz with a duty cycle not exceeding 45%. In addition, in the preferred embodiment, it is important that the power supply 58 (FIG. 9) not be allowed to operate with duty cycles approaching 50% which would cause a failure in the transistor 282 from excessive current. The PWM signal is present unless the shutdown pin S/D of the PWM chip 162 goes high. During normal operation, the PWM signal is pre-empted by the synchronized VCNTL signal as required to regulate the output voltage.

A second input to the shutdown pin S/D of the PWM chip 162 originates from a current control section (FIG. 10b). The current control section comprises a pair of amplifiers 286, 288 and a comparator 150. The comparator 150 monitors the peak current from the current sensor 151 (FIG. 9) and compares it to a reference voltage derived from the DAC reference voltage. If the peak primary current of the primary winding of the flyback transformer 180 exceeds the DAC reference voltage, the comparator 150 output goes high and causes the PWM signal to shutdown. The purpose of the current sense circuit 151 is to prevent the primary current of the flyback transformer 180 from attaining values which result in saturation. The DAC reference voltage applied to the comparator 150 is filtered by capacitor 292. The DAC voltage is further buffered by amplifier 288, scaled by a pair of resistors 281, 283 and presented to clamp amplifier 286. The clamp amplifier 286 provides a variable current limit threshold as a function of the DAC voltage. The clamp amplifier 286 clamps the voltage at the comparator input 150 to approximately 1.9 V for DAC voltages above 3.0 V. The clamping action is produced by a diode and resistor arrangement 302, 304, 306, 308. The reference voltage is determined by divider resistors 306, 308, diode 304 drop and a 5.1 reference voltage from the PWM controller 162. The current sense circuit 151 limits the amount of energy that can be delivered to the secondary winding of the flyback transformer 180 which prevents excessive overshoot during periods of light or no loads.

RF POWER AMPLIFIER

Figure 11:
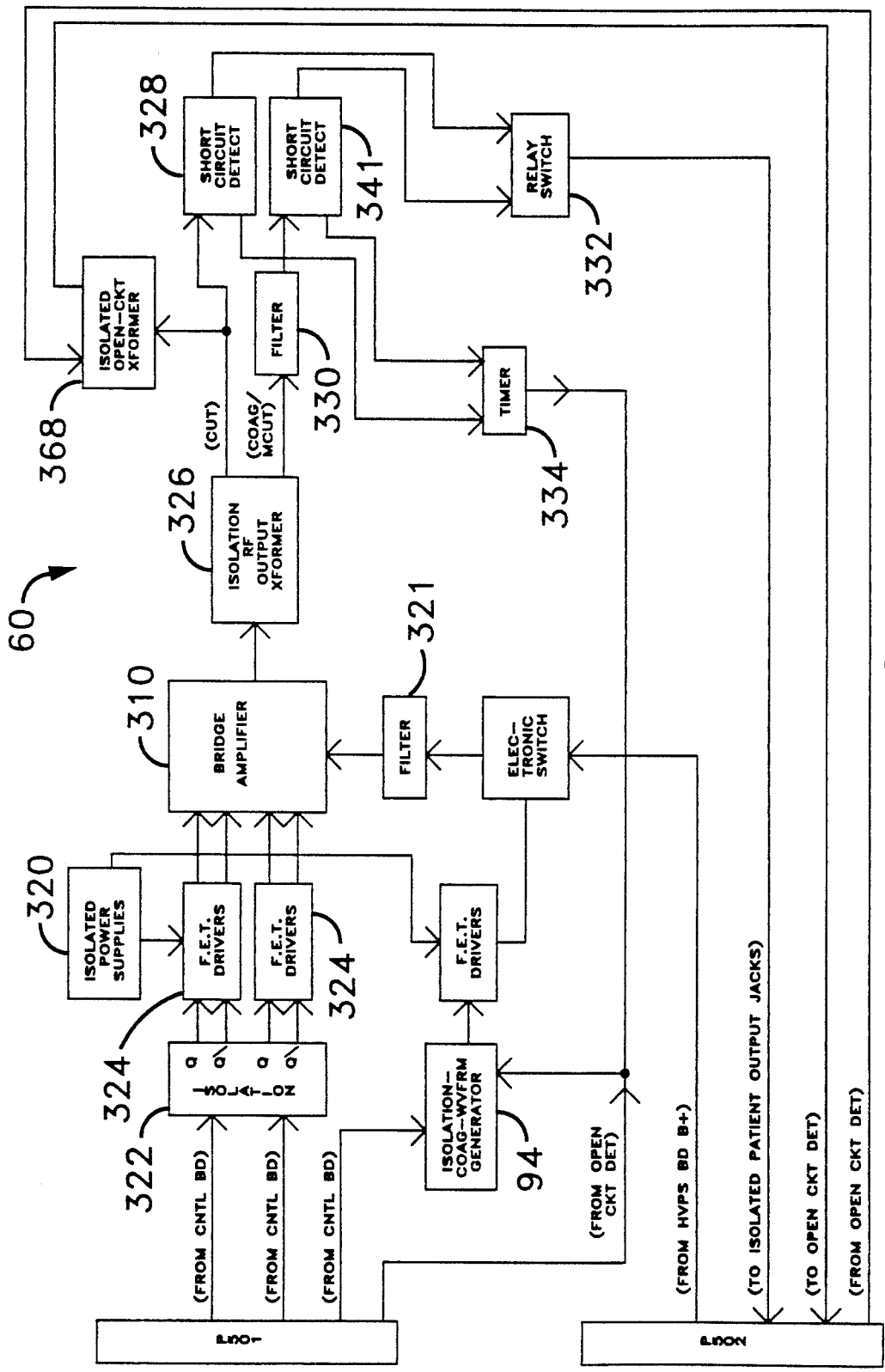
FIG. 11 is a general block diagram of an RF power amplifier printed circuit board of the bipolar RF generator of FIG. 1.

Referring to FIG. 11, there is shown a general block diagram of the RF power amplifier board 60 in accordance with the present invention. The bridge amplifier 310 is capable of doubling the output voltage for a given voltage signal received from the high voltage power supply board 58. Signals from the 1 MHz split phase dead zone generator 106 (FIG. 7) are supplied to an isolation circuit 322 which isolates the bridge amplifier 310 from low level driver circuitry associated with the bridge amplifier 310. The output voltage signal from the power supply board 58 (FIG. 9) is also transmitted to a coagulation waveform generator 94, the driver for which is located on the controller board 54 (FIG. 4). The coagulation waveform generator 94 receives three signals: the voltage signal from the power supply board 58, an isolated power supply source 320 and a modulating signal. When the RF generator is in the cut mode, the output voltage signal from the power supply board 58 (FIG. 9) is transmitted unaltered by the modulating signal through the coagulation waveform generator 94.

Figure 12:
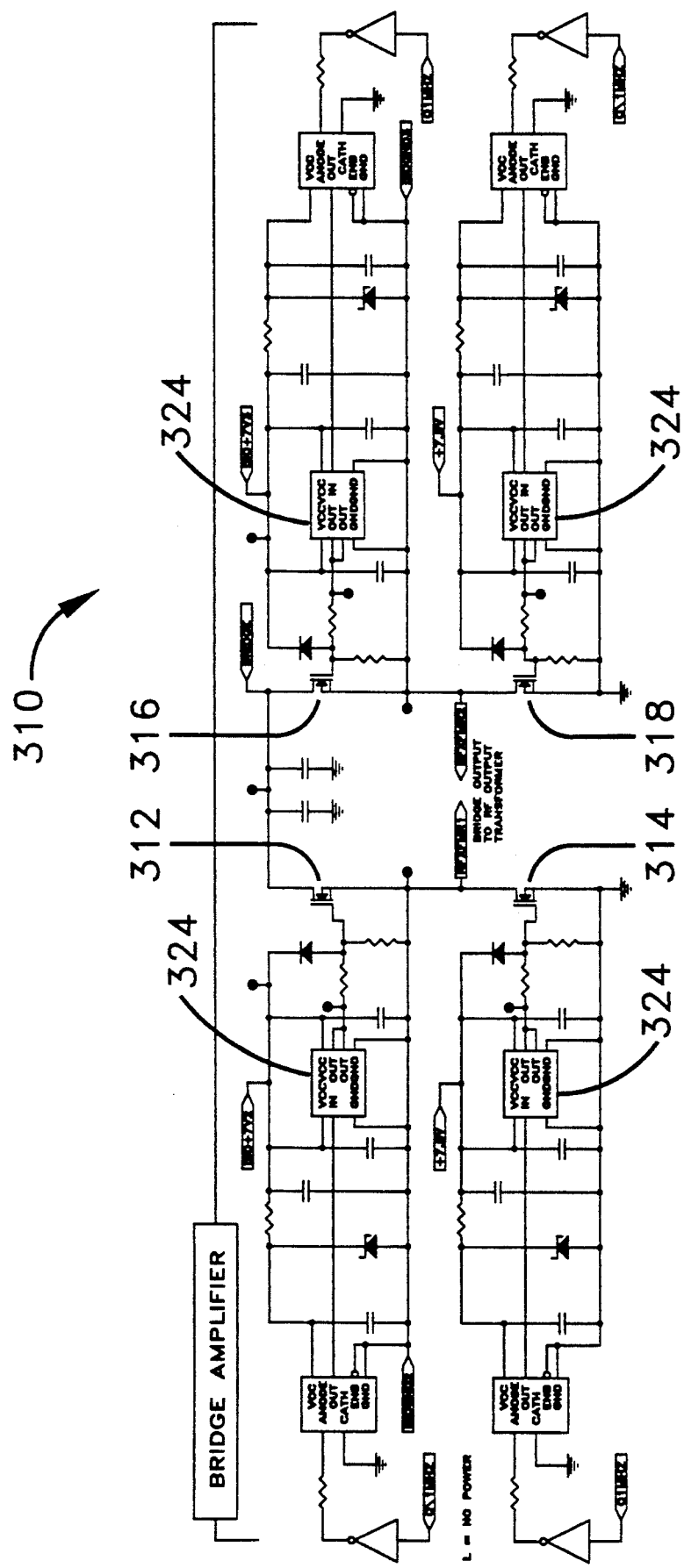
FIG. 12 is a circuit schematic of a bridge amplifier of the RF power amplifier of FIG. 11.

During the coagulation mode, the output voltage signal from the power supply board 58 (FIG. 9) is modulated by the modulation signal to form an asynchronous sinusoidal coagulation waveform as discussed above. The modulated voltage signal is then transmitted to a plurality of FET drivers 324 associated with the bridge amplifier. The FET drivers 324 drive the bridge amplifier 310 at a 1 MHz rate. The bridge amplifier 310 is preferably of an H design and comprises four drivers 312, 314, 316 and 318 (see FIG. 12). The drivers 312, 314, 316 and 318 are paired together such that one pair comprises drivers 312 and 318 and the second pair comprises driver 314 and 316. The pairs of drivers are alternately fed out of phase 1 MHz signals by the FET drivers 324. Isolated power supplies 320 isolate the bridge amplifier drivers 312 and 316, which are non-ground referenced, from drivers 314 and 318, which are ground referenced. A noise filter 321 smoothes out the signal generated by the coag waveform generator 94 by removing the high frequency components.

The voltage signal formed by the bridge amplifier is either a damped sinusoidal signal having random bursts for coagulation or a normal sinusoidal signal for cut, both of which are controlled by the microprocessor 70 (FIG. 4). The damped or normal sinusoidal signal is transmitted from the bridge amplifier 310 to an isolation RF output transformer 326. The microprocessor 70, the coag waveform generator 94, relay 333, relay 335 and RF output transformer 326 determine if the generated waveform is a cut waveform or a coagulation waveform and the impedance of each. In the preferred embodiment, a cut waveform has a relatively high impedance which is generally less than 300 ohms and the coagulation waveform has a generally low impedance which is preferably less than 20 ohms.

A generated cut waveform is transmitted to an isolated open circuit detection transformer 368 for preventing excessively high voltage from being transmitted to the surgical pen 38 during periods when the surgical pen 38 is in an open state. The cut waveform is also transmitted to a short circuit detect circuit 328 which determines when the cut waveform current exceeds a predetermined threshold.

A generated coagulation waveform is transmitted to a filter 330 which filters the coagulation waveform. The filtered coagulation waveform is transmitted to a second short circuit detect circuit 341. The second short circuit detect circuit 341 determines when the coagulation waveform exceeds a predetermined threshold current. If the cut waveform or the coagulation waveform exceed the threshold current of the respective short circuit detect circuit 328 or 341, a timer 334 is enabled which disables power to the bridge amplifier 310 through the coag waveform generator 94. The timer 334 operates at 100 millisecond intervals and is disabled at the end of the 100 millisecond period to test the RF power at the bipolar pen 38 to determine if the shorted conditions still exists.

Figure 13:
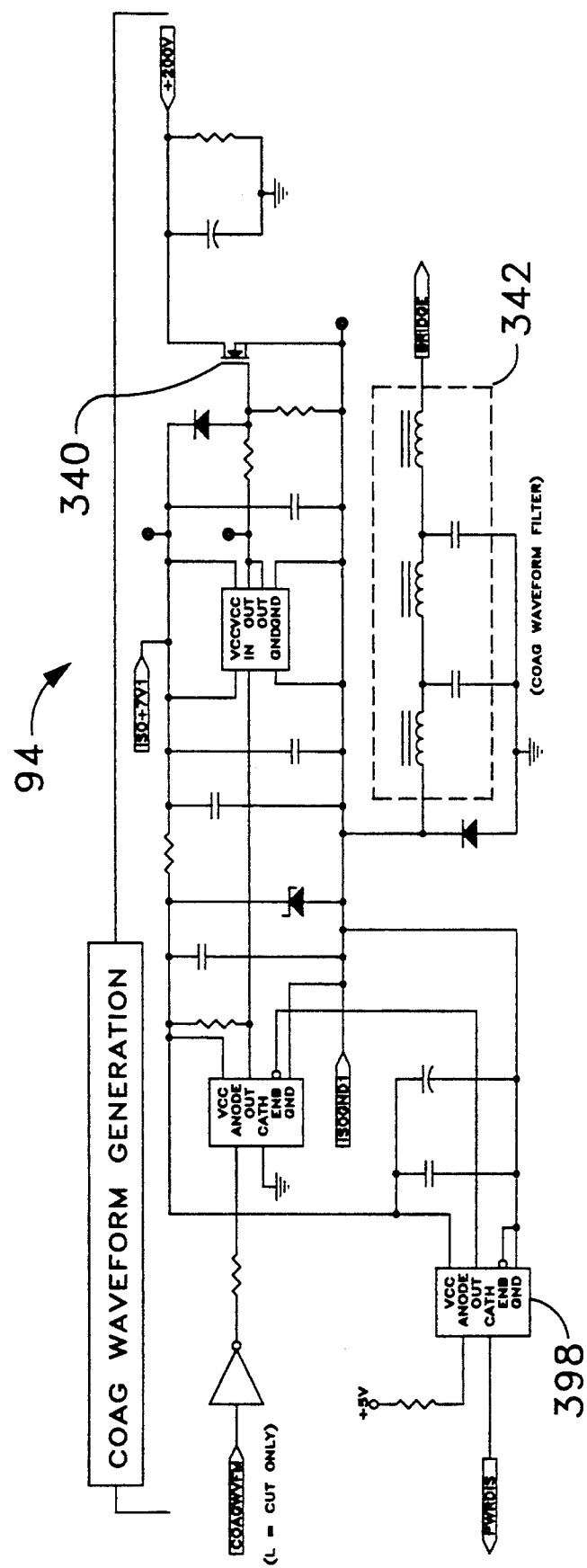
FIG. 13 is a circuit schematic of a coagulation waveform generation circuit of the RF power amplifier of FIG. 11.

Referring to FIGS. 12-16, there are shown more detailed circuit schematics of various circuits located on the RF power amplifier board 60. A bridge amplifier 310 (FIG. 12) generates a waveform at a 1 MHz rate. The bridge amplifier 310 is preferably of an H design and comprises four driving devices: 312, 314, 316 and 318. The driving devices 312, 314, 316 and 318 are situated such that driver 312 is above driver 314 and driver 316 is above driver 318 and further such that driver 312 is in facing relationship with driver 316 and driver 314 is in facing relationship with driver 318. The drivers 312, 314, 316 and 318 are divided into pairs such that one pair comprises drivers 312 and 318 and the second pair comprises drivers 314 and 316. The pairs of drivers are alternately fed out of phase signals by FET drivers 324 at a 1 MHz rate such that at any given point in time one pair of drivers is on and the other pair of drivers is off. A voltage is supplied to drivers 312 and 316 from the high voltage power supply board 58 through the coagulating waveform generator 94 (FIG. 13). Each time the driver pairs are reversed, the voltage generated across an isolated RF output transformer 326 (FIG. 14) is doubled.

A trio of floating or isolated power supplies 320 (FIG. 15a) are connected to either side of the upper half of the bridge amplifier 310 and the coag waveform generator 94 for isolating the bridge amplifier 310 and coag waveform generator 94 from low level driver circuitry. Each of the isolated power supplies 320 includes a common self-oscillating transformer supply.

The RF output transformer 326 (FIG. 14) is preferably a nickel-zinc transformer which forms a sine waveform. A DC blocking capacitor 338 is associated with the transformer 326 to prevent saturation of the transformer core. There is a direct relationship between the voltage input into the bridge amplifier 310 and the voltage output. If a low voltage is transmitted to the bridge amplifier 310, there is a low voltage output. Similarly, if there is a high voltage transmitted to the bridge amplifier 310, there is a high voltage output.

The RF bridge amplifier 310 is powered by a DC voltage from the high voltage power supply board 58 which is modulated by the coag waveform generator 94. The DC voltage to the RF bridge amplifier 310 is controlled by the DAC voltage which also controls the output voltage of the high voltage power supply board 58 and may be further controlled by a coag waveform signal delivered to the coag waveform generator 94 from the controller board signal COAGWVFM. In the preferred embodiment, the coag waveform signal driver 340 (FIG. 13) is a MOSFET transistor. If the bipolar generator is in the cut mode, the coag waveform signal driver 340 is fully saturated, which allows for the voltage to travel from the power supply board 58 directly to the RF bridge amplifier 310.

Referring to FIG. 13, during the coag mode, the coag waveform generator 94 modulates the voltage supplied by the power supply board 58. The modulated DC voltage passes through a series of capacitors and inductors which act as an LC filter 342. The resulting signals from the LC filter 342 form a damped sinusoidal signal which is transmitted to the RF bridge amplifier 310.

Figure 14:
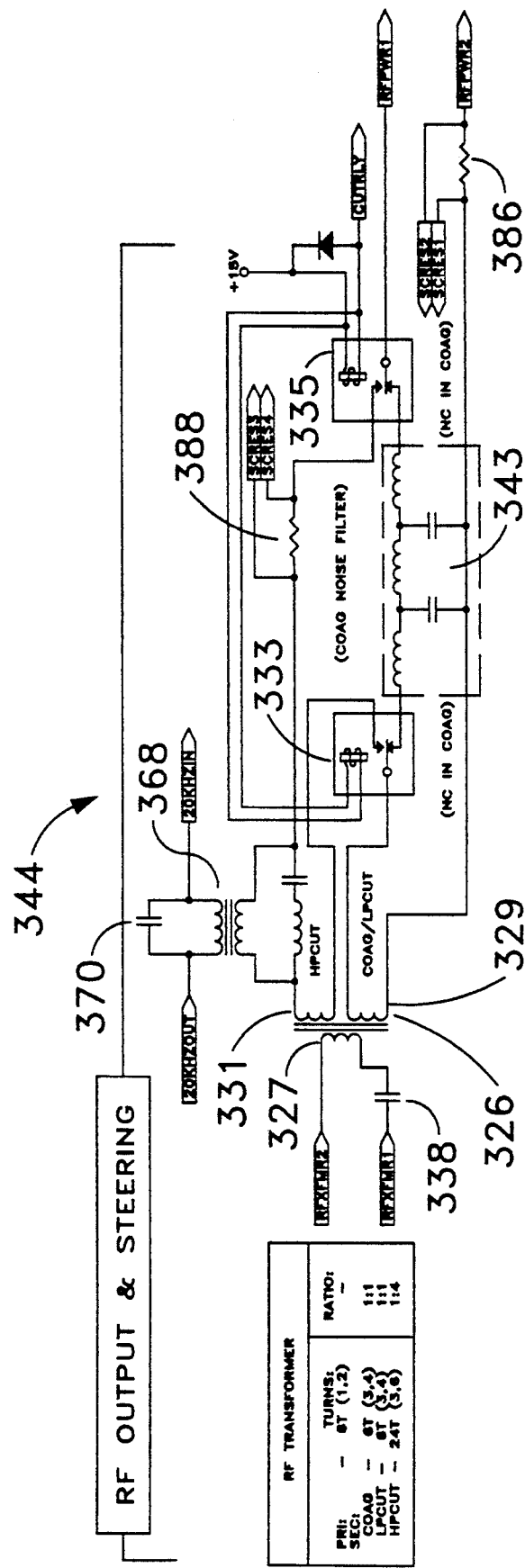
FIG. 14 is a circuit schematic of a RF output and steering circuit of the RF power amplifier of FIG. 11.
Figure 15A:
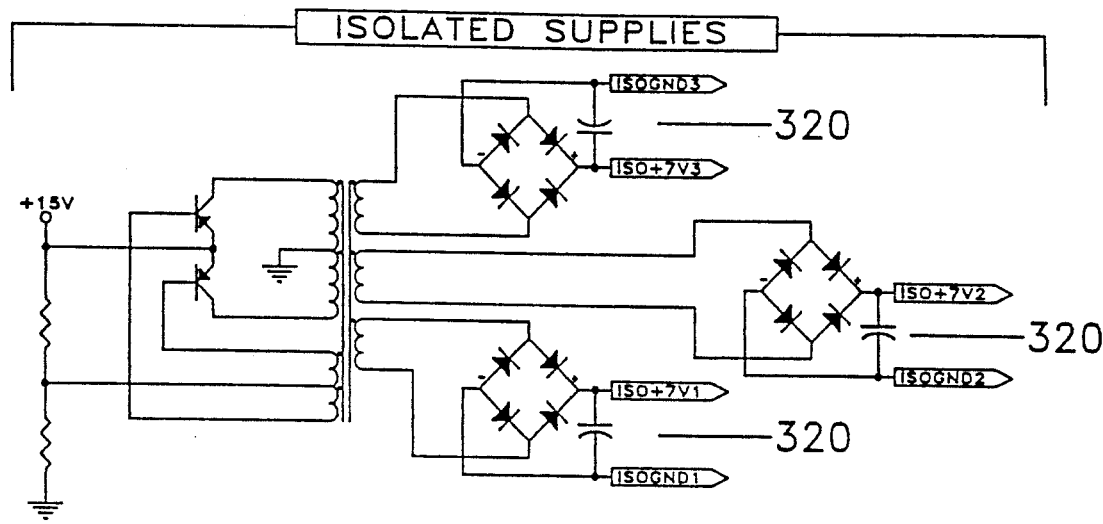
FIGS. 15a-15b are circuit diagrams of portions of isolated supplies of the RF power amplifier of FIG. 11.
Figure 15B:
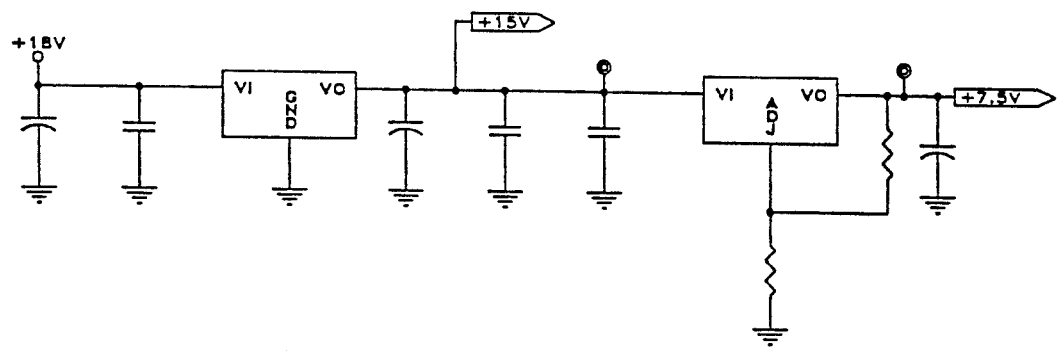

Referring to FIG. 14, an RF output and steering circuit 344 is provided for filtering noise from the coag signal and for sensing the current output at the bipolar pen 38. The RF output and steering circuit 344 comprises an RF output transformer 326, having a primary winding 327 and two secondary windings 329, 331 and two relays 333 and 335. The primary winding 327 is connected in series with a DC blocking capacitor 338 which prevents the RF transformer 326 from reaching a saturation point. A first secondary winding 329 of the RF transformer is a low impedance winding and the second secondary winding 331 is a high impedance winding. Switching of the secondary windings 329, 331 is controlled by a pair of relays 333, 335 and a cut relay signal CUTRLY which is generated by the microprocessor 70.

The coag and microcut modes require a low impedance which preferably is less than 20 ohms. The high power cut mode requires a higher impedance which is generally less than 300 ohms. When necessary, secondary winding 331 is added in series to secondary winding 329 to achieve a higher impedance. By disconnecting the two secondary windings 329, 331, the amount of high voltage energy generated in the high power cut winding 331 can be isolated when the coagulation mode is activated. The high voltage energy generated produces excessive noise which can create interference problems both within and outside of the housing of the bipolar generator. A coag noise filter 343 provides harmonic signal suppression and allows for proper matching between the RF output transformer 326, the bipolar instrument cord 46 and the biological loading at the bipolar pen 38.

Figure 16:
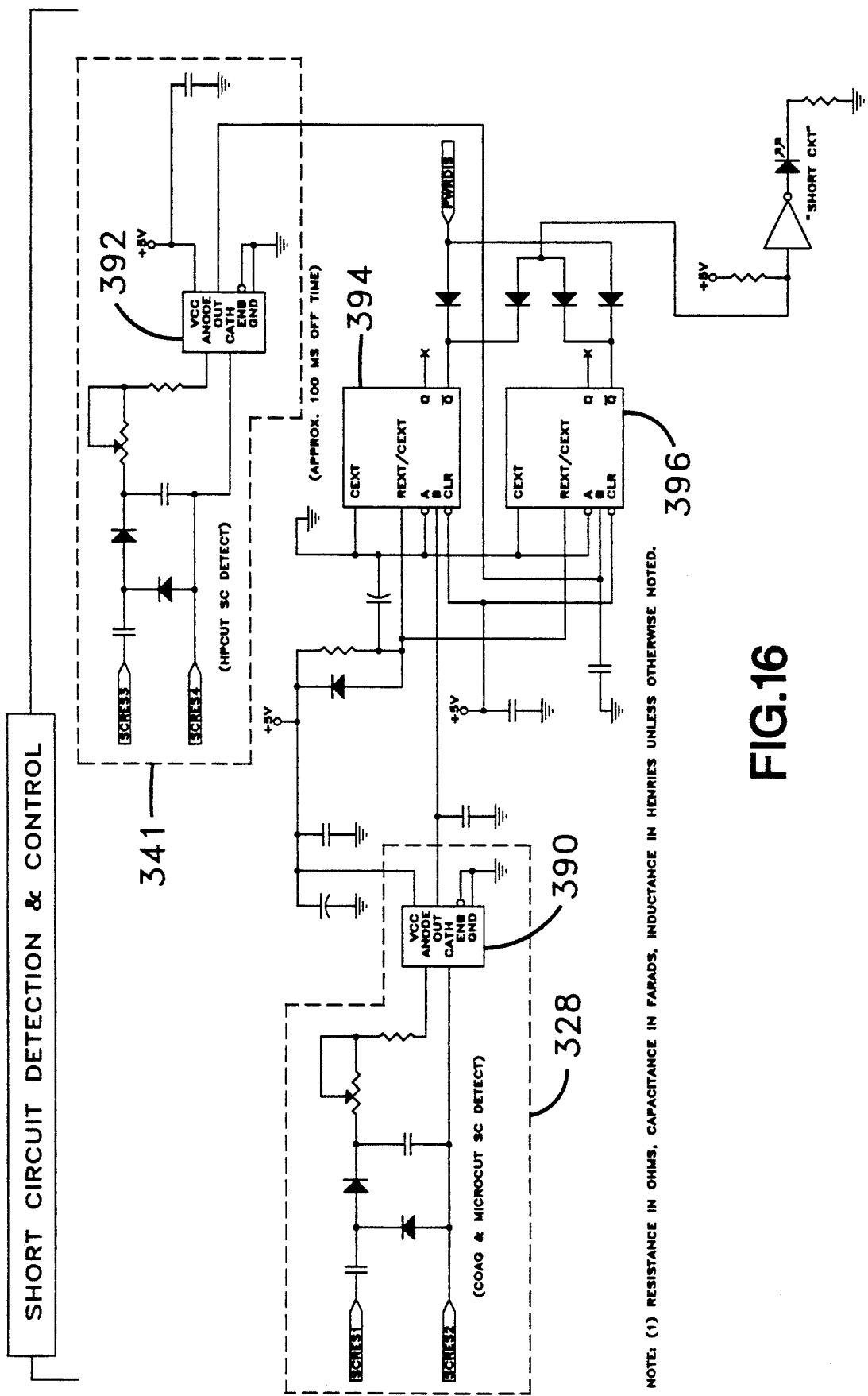
FIG. 16 is a circuit schematic of a short circuit detect circuit of FIG. 11.
Figure 19:
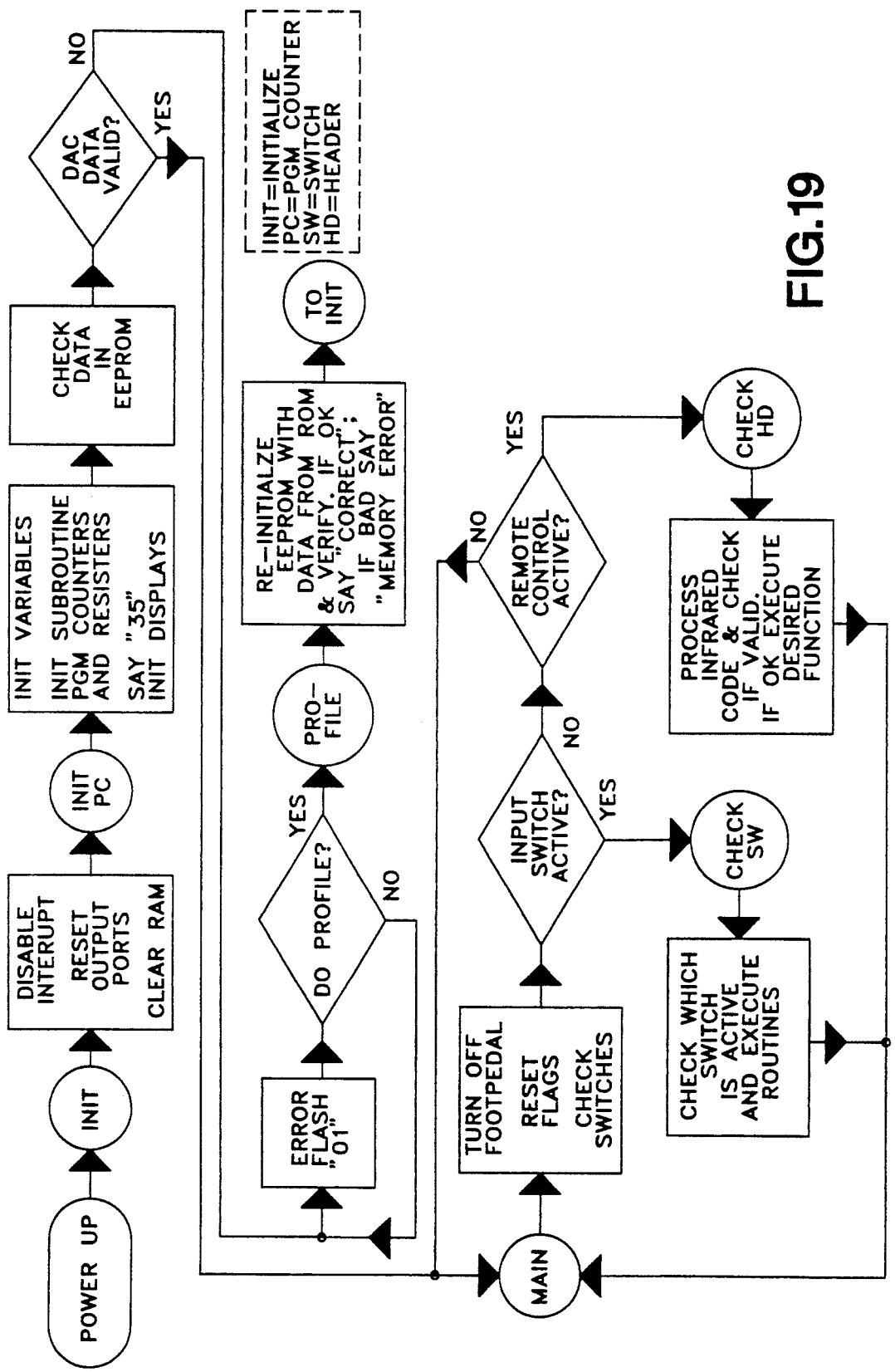
FIG. 19 is a flow chart depicting a synopsis of the software operation.
Figure 20A:
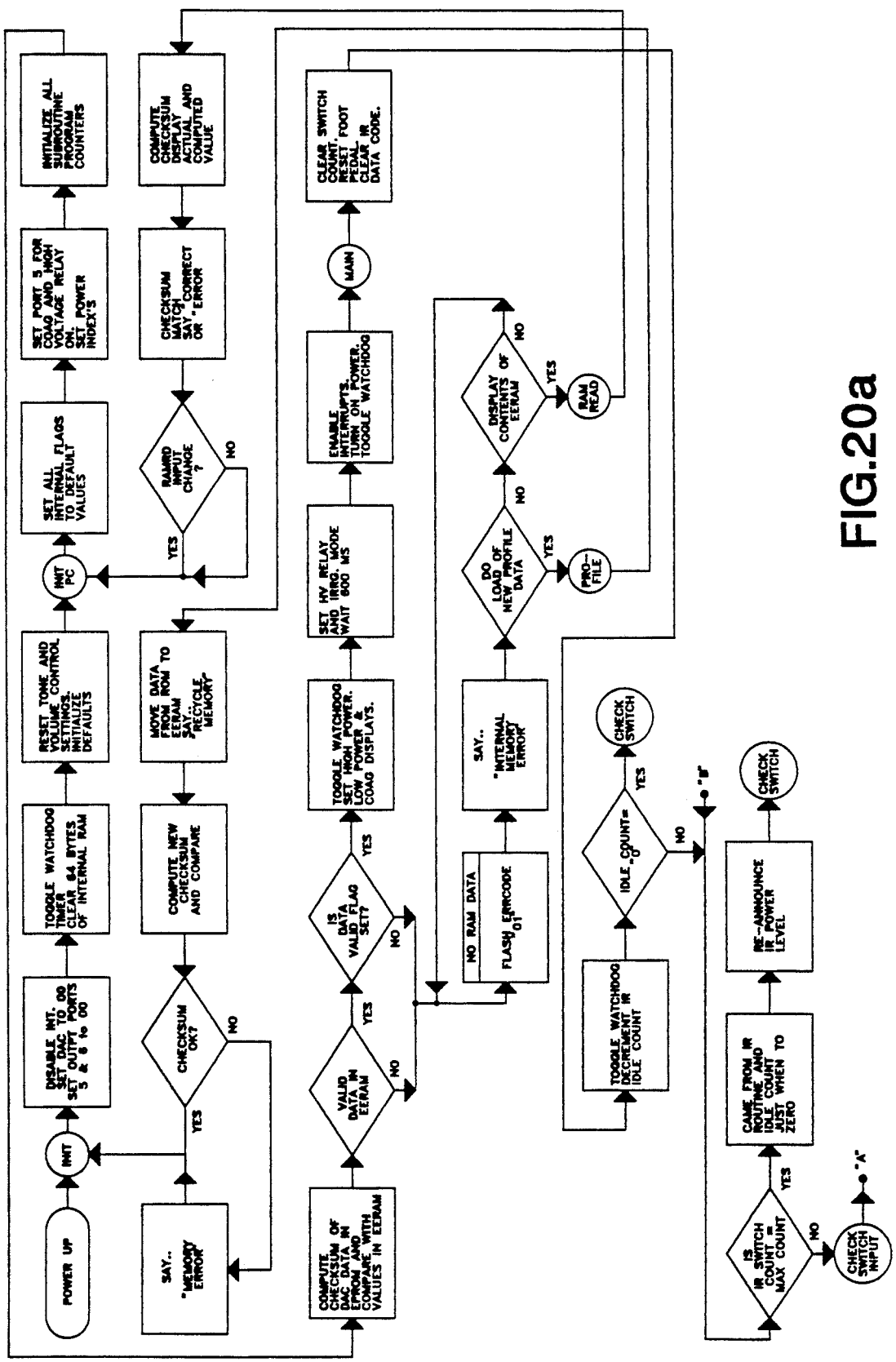
FIGS. 20a-20k are flow charts depicting the details of the software operation.
Figure 20B:
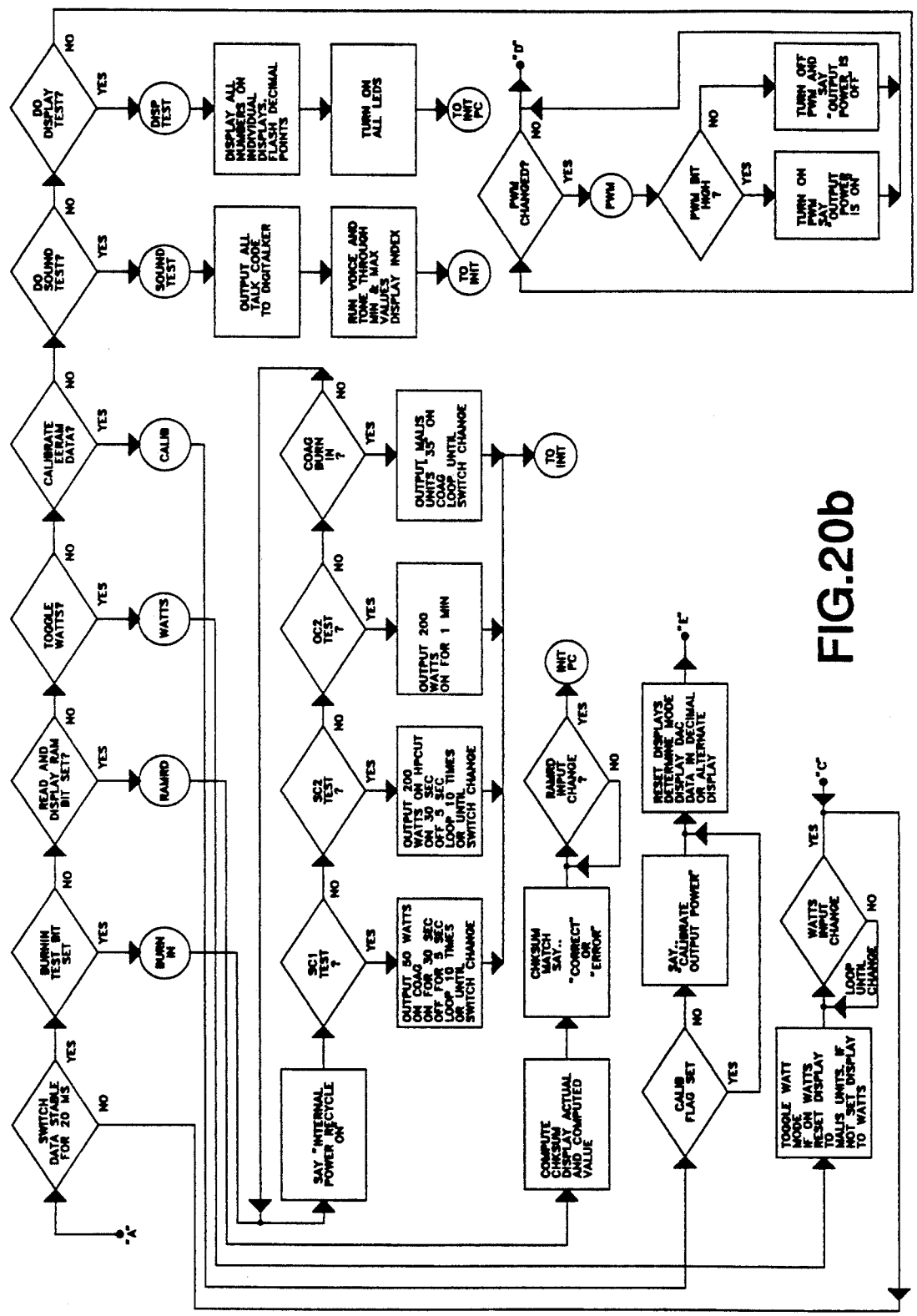
Figure 20C:
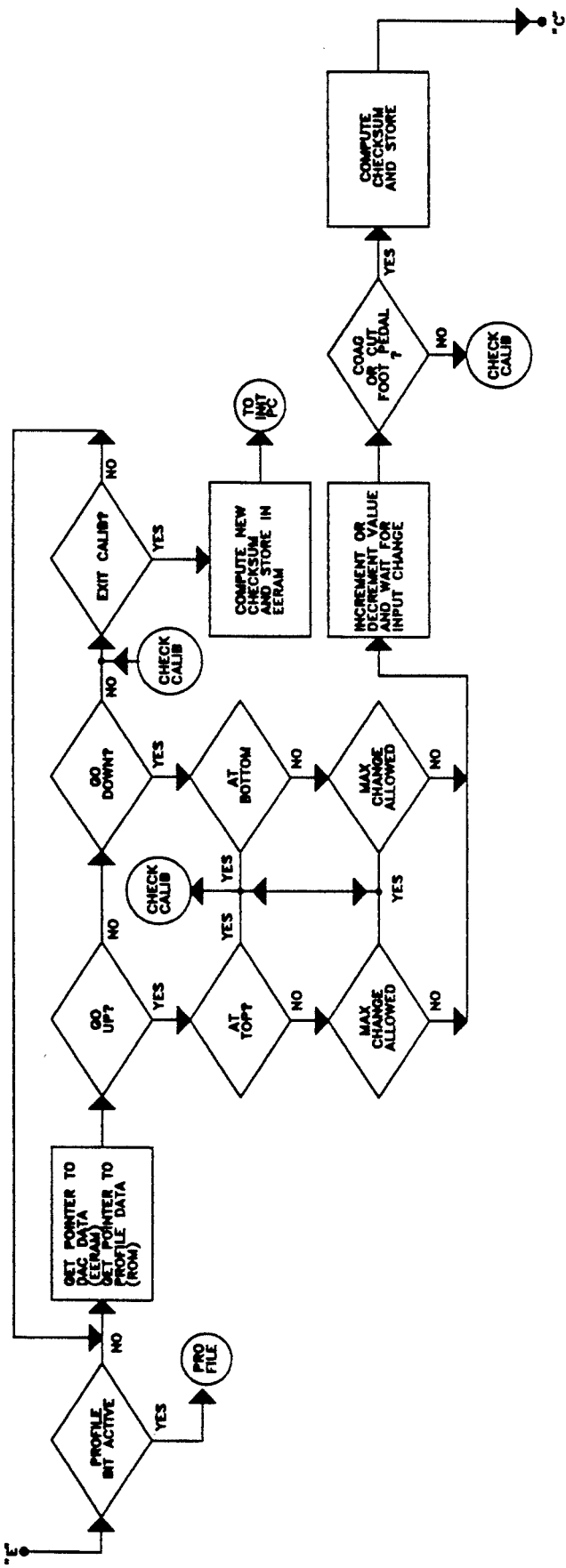
Figure 20D:
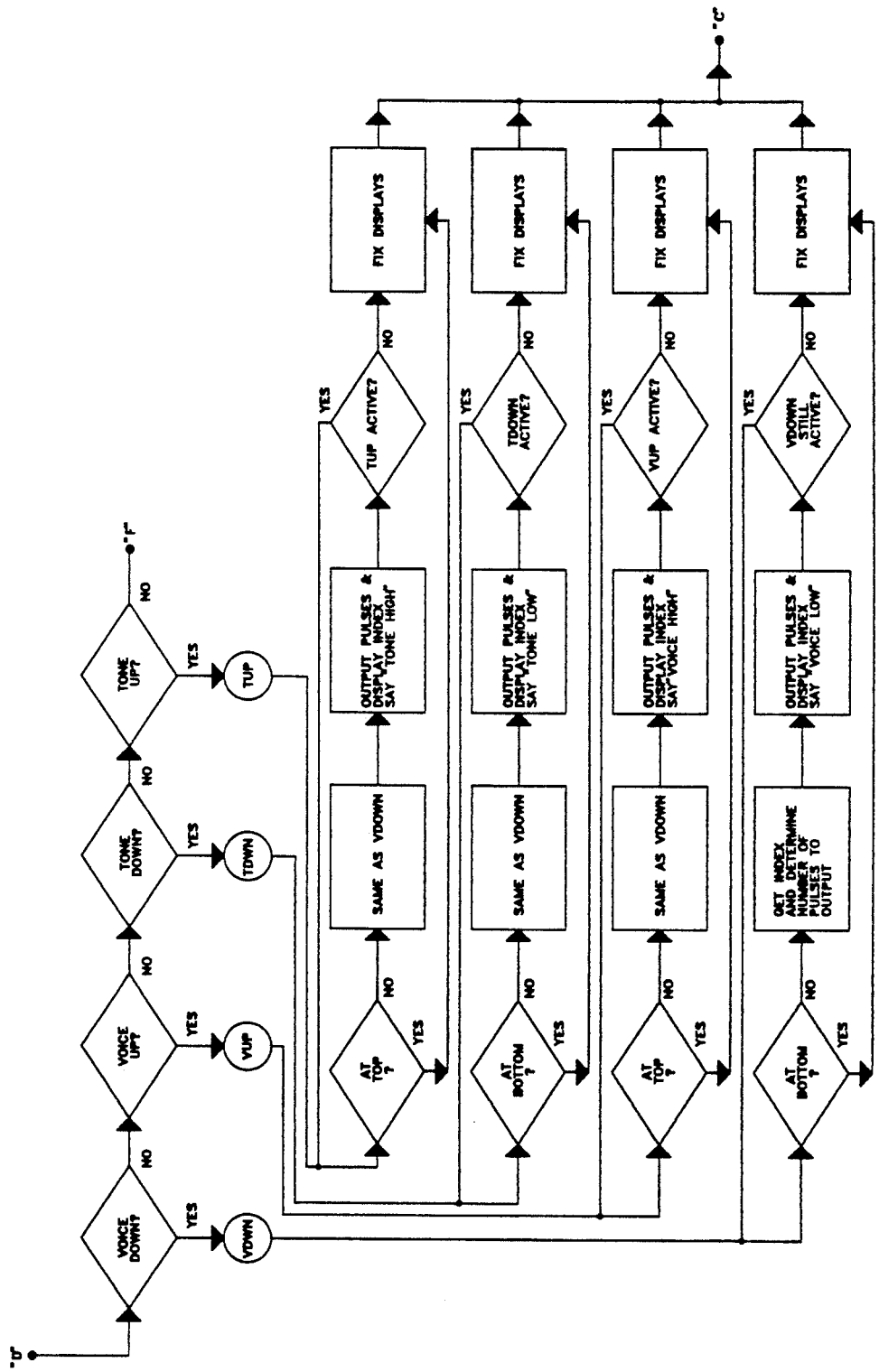
Figure 20E:
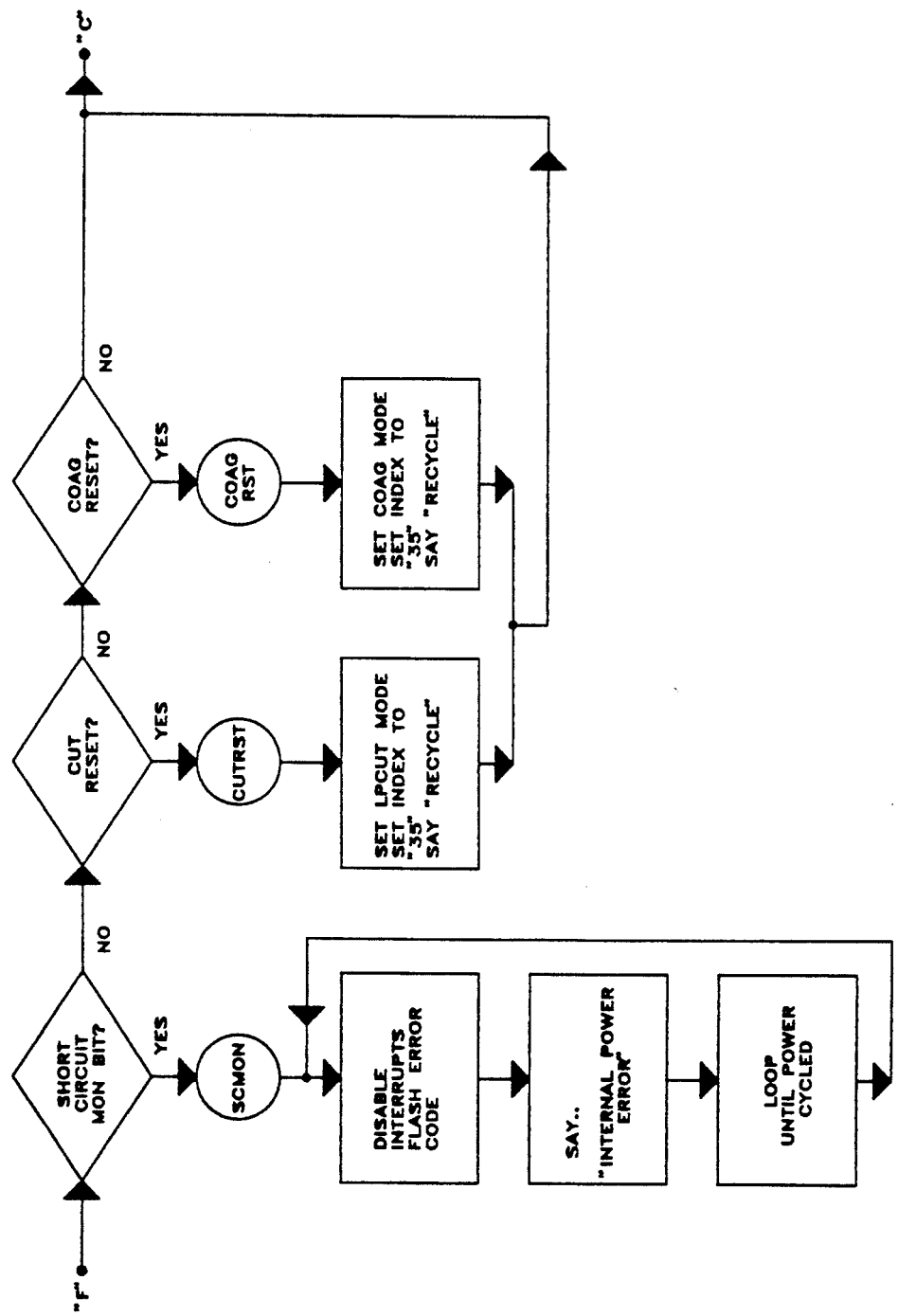
Figure 20F:
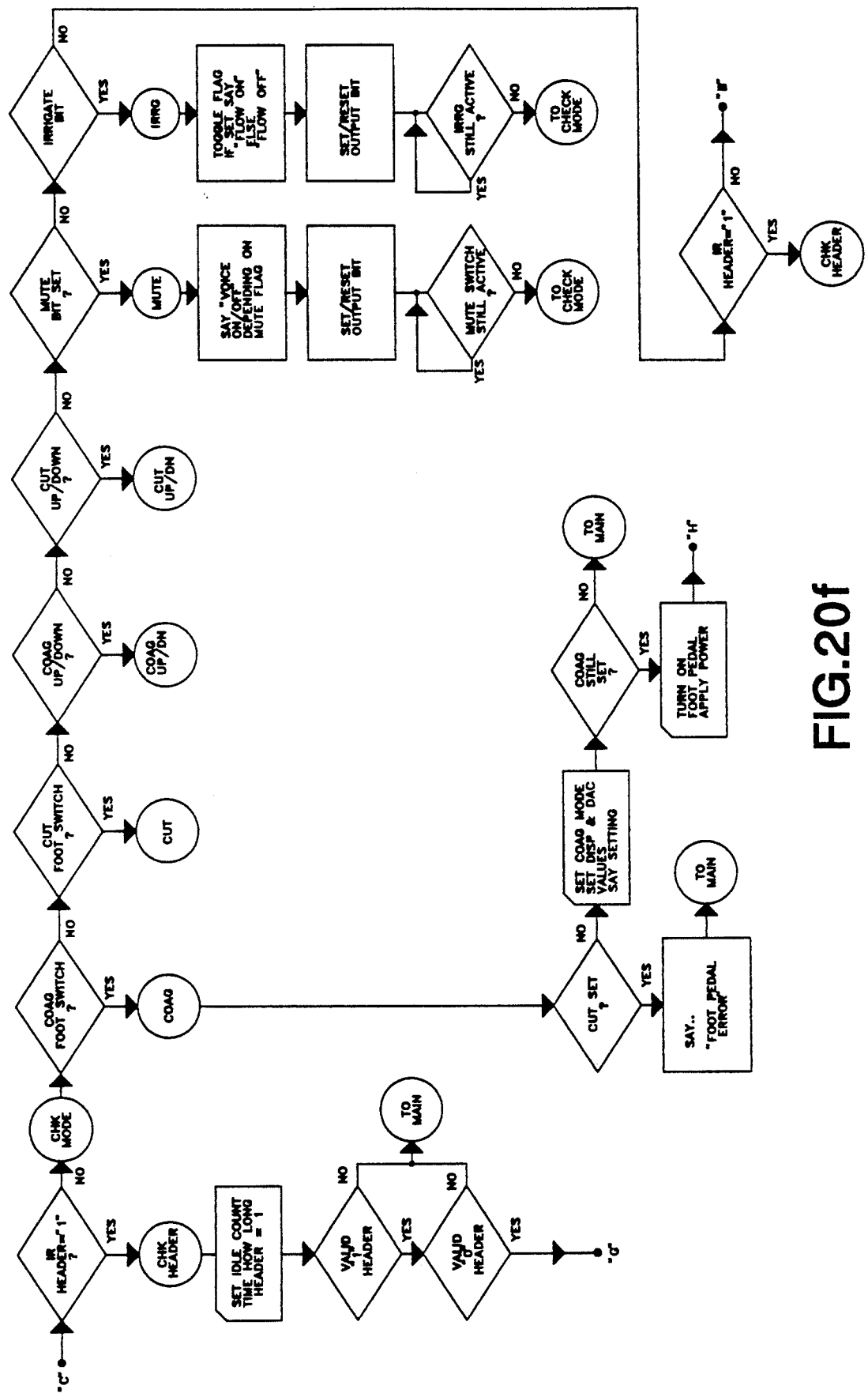
Figure 20G:
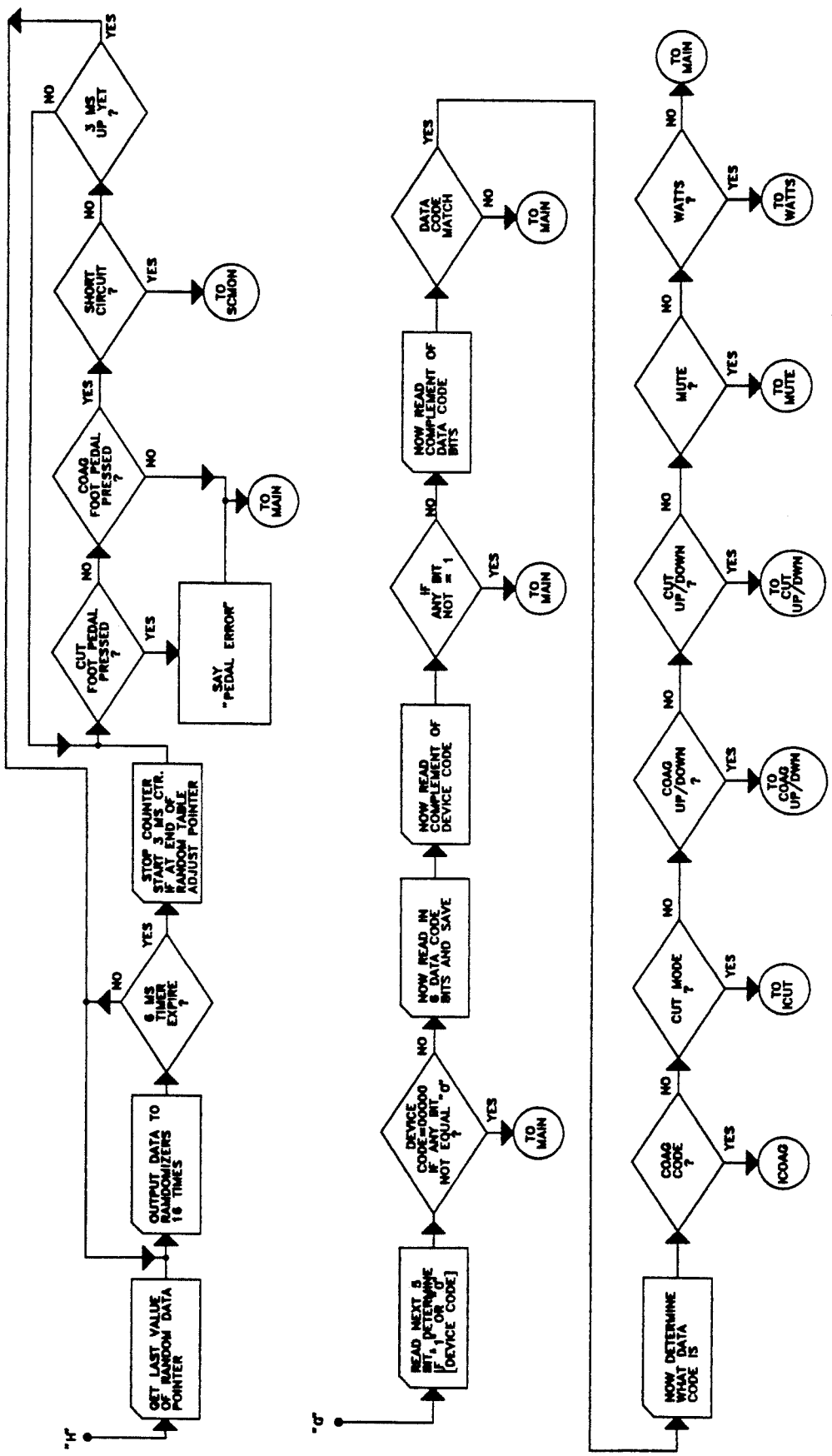
Figure 20H:
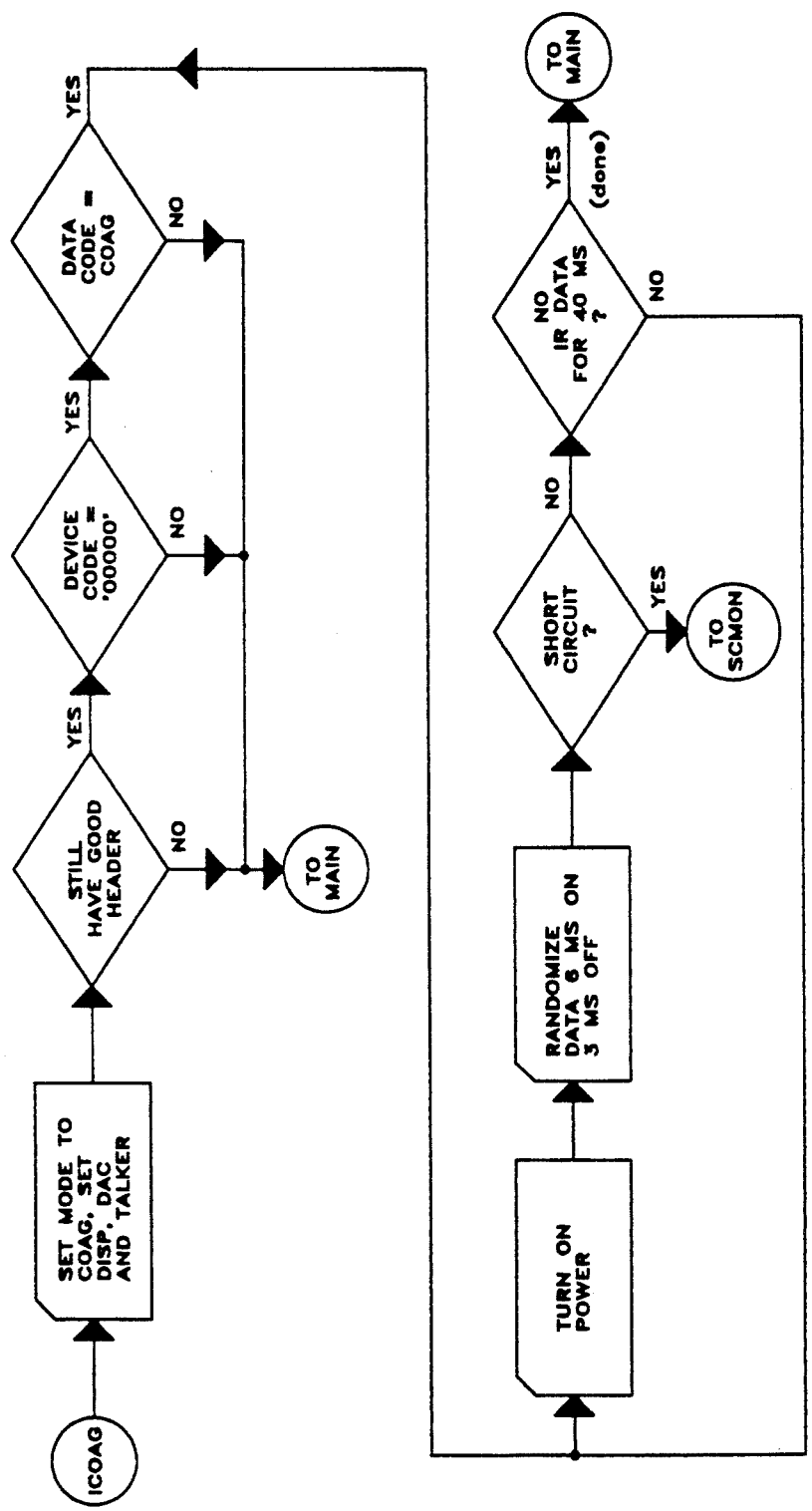
Figure 20I:
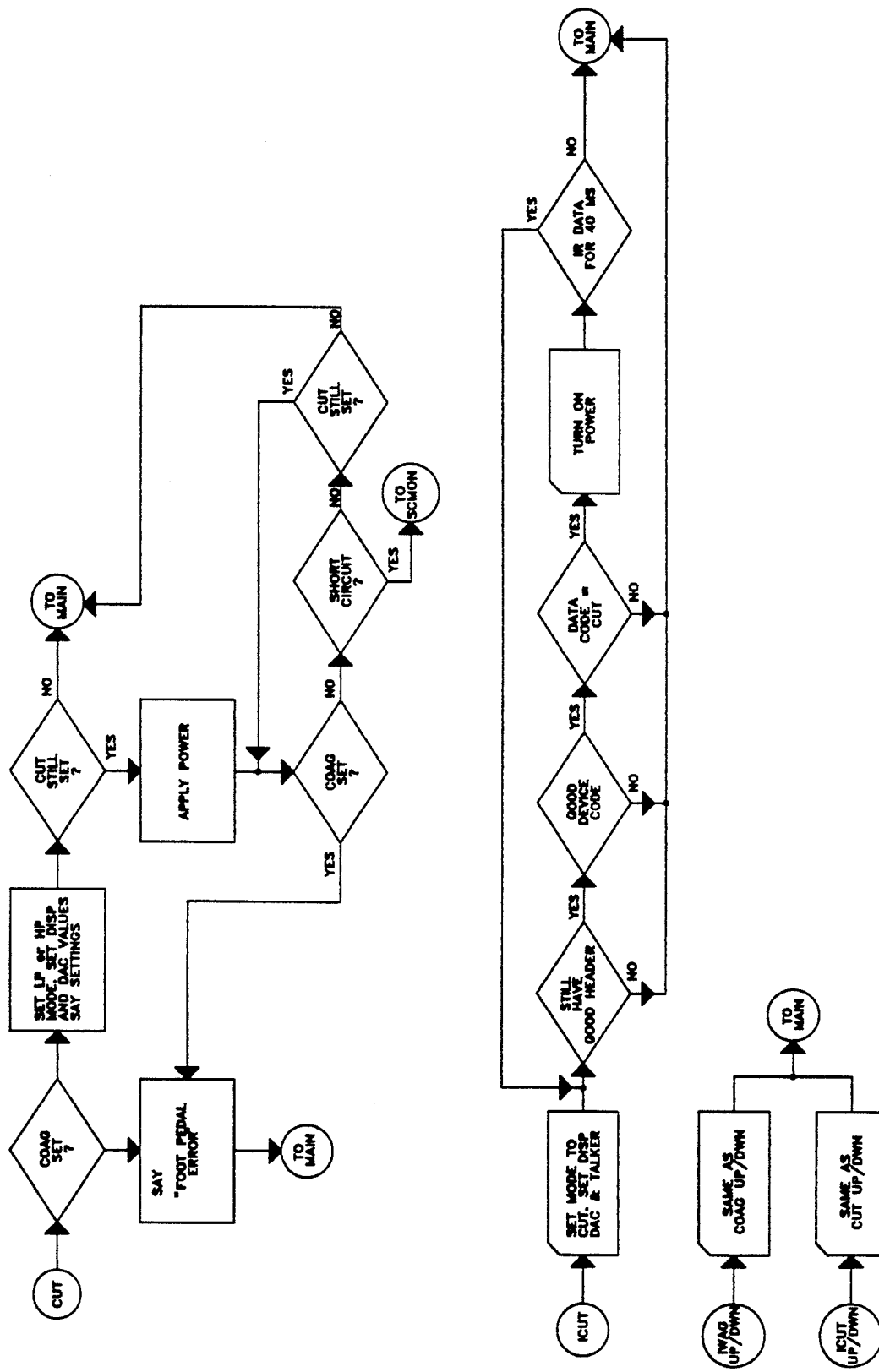
Figure 20J:
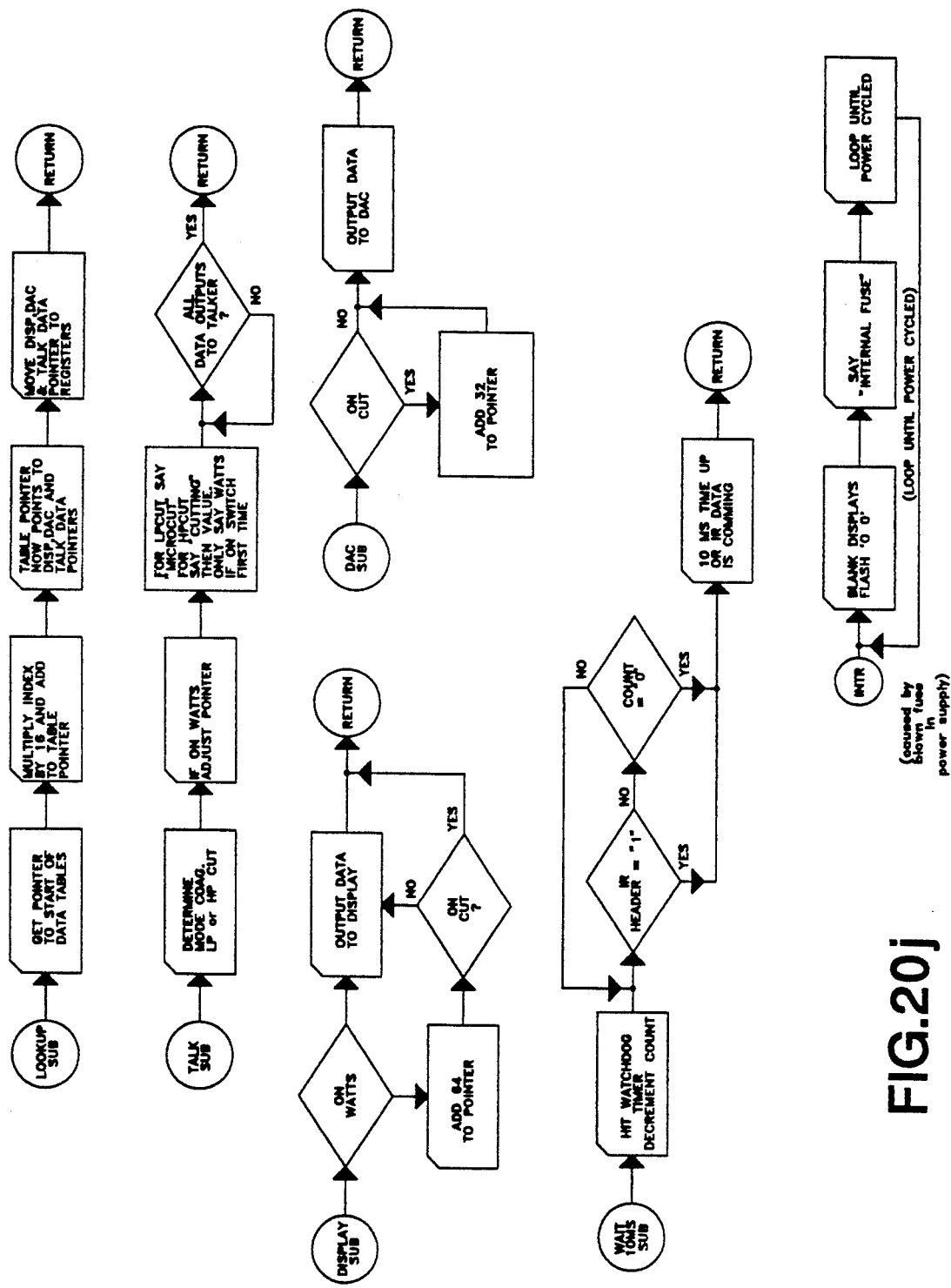
Figure 20K:
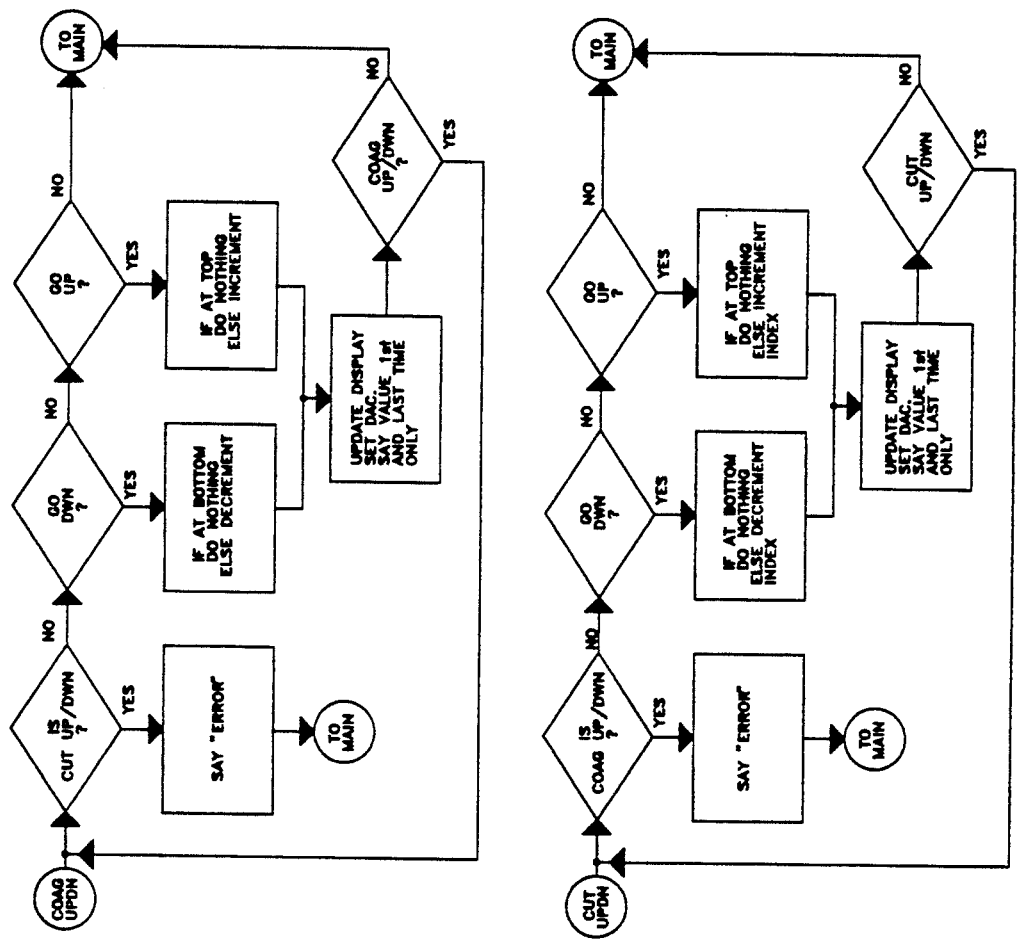

Referring to FIG. 16, a pair of short-circuit detection circuits 328, 341 are provided for detecting a short circuit at the bipolar pen 38 while the bipolar generator is in use. A first short-circuit detection circuit 328 is used to detect short circuits during the coag or microcut mode. The second short-circuit detection circuit 341 is used to detect short circuits which occur during the high power cut mode. A first resistor 386 (FIG. 14) senses the current through the bipolar pen 38 when the RF generator is in the coag or microcut mode. A second resistor 388 (FIG. 14) senses the current through the bipolar pen 38 when the RF generator is in the high power mode. The sensed current is perceived by the short-circuit detection circuit in the form of a small voltage. A pair of optoisolators 390, 392 rectify and filter the received voltage signals. When a predetermined threshold voltage is exceeded, the optical isolators 390, 392 conduct indicating a short-circuit condition exists. The optoisolators 390, 392 each transmit a voltage signal to one-shot timers 394, 396. When the one-shot timers 394, 396 detect the received voltage signal, they begin to generate output pulses at 100 millisecond intervals as long as a short-circuit condition exists. The output signals from the one-shot timers 394, 396 of each of the short-circuit detection circuits 328, 341 are ORed together to form a power disable signal PWRDIS. During each 100 millisecond timing period, the voltage signal to the RF bridge amplifier 310 is cut off. At the end of each 100 millisecond period, the RF power is restored to the RF bridge amplifier 310 to determine whether the shorted condition still exists. The circuitry continues to cycle in this manner until the short-circuit condition is removed.

The power disable signal PWRDIS is also shared by an open circuit detector 354 (FIG. 17b) which will be described in detail hereinafter. The short-circuit detection circuits 328, 341 prevent excessively high RF currents from destroying the RF power amplifier board 60 and the bipolar pen 38.

MOTHER BOARD

Referring specifically to FIGS. 17a, 17b, 18a, 18b, 18c and 18d, the mother board 50 comprises a low voltage power supply 350, an infrared remote control receiver 352, an open circuit detector 354, pneumatic foot switches 356, tone and voice volume control switches 358, and all card edge connectors (not shown) necessary for joining the above-described printed circuit boards.

In the preferred embodiment, the low voltage power supply 350 produces four low voltages which are supplied from the mother board 50 to the other boards. Two of the voltages produced are regulated and other two voltages produced are unregulated. In the preferred embodiment, the regulated voltages comprise a +5 VDC at 2 amps voltage and a +15 VDC at 1 amp voltage. The unregulated voltage comprises a +18 VDC at 1 amp voltage and a −18 VDC at 0.1 amp voltage. The structure and operation of the low voltage power supply 350 is typical of all such supplies and need not be described in detail.

An infrared remote control receiver 352 monitors activity from a hand held infrared remote control transmitter (not shown). The infrared remote control receiver 352 receives remote control signals from the transmitter, converts the infrared signals into electrical signals, and transmits the received serial data to the microprocessor 70 for processing. It is to be understood by those skilled in the art that the infrared remote control transmitter and infrared remote control receiver 352 operate in a conventional manner and will not be discussed in further detail.

A pair of pneumatic foot pedals (not shown) are associated with the RF generator. A first foot pedal is used during the coag mode and a second foot pedal is used during the cut mode. A pair of foot switches 356a, 356b, located on the mother board 50 are associated with each foot pedal. In the preferred embodiment, the foot switches 356a, 356b are pneumatic switches. Air pressure produced from the cut and coag foot pedals pressurize the respective foot switches 356a, 356b. Data signals corresponding to the received air pressure are transmitted to the microprocessor 70 for processing.

Tone and voice volume control switches 358a, 358b of a standard type well known in the art which control the tone volume and voice volume of the audio signals produced by the sound board 56 are located on the front panel 10 of the RF generator and are mounted on the mother board 50. The received tone volume and voice volume signals are transmitted to the microprocessor 70 for processing.

An open circuit detector (OCD) 354 is mounted on the mother board 50 and is interfaced with certain elements located on the RF power amplifier printed circuit board 60. The OCD 354 prevents excessively high cutting voltages which can occur and result in the break down of components in the RF path. The OCD 354 also eliminates the occurrence of RF interference during periods when cutting is not actually occurring.

Referring to FIG. 17a, an audio signal preferably less than 3 volts peak-to-peak and approximately 20 KHz is generated by a waveform generator 362. The generated 20 KHz signal is preferably in the form of a sine wave. The generated audio signal is buffered by a transistor 364 and capacitor 366 and is coupled to a transformer 368 and second capacitor 370 located on the RF output and steering circuit (FIG. 14) of the RF power amplifier board 60. The processed audio signal results in a 20 KHZOUT pin signal. The primary winding of the transformer 368 and the second capacitor 370 form a parallel resonant circuit.

A 20 KHZIN signal travels through a filter 372 (FIG. 17b), a buffer 374, a detector 376 and a threshold comparator 378. If an open circuit condition exists, such as when the tips of the bipolar pen 38 are in an open state, which is detected by the secondary winding of the transformer 368, the resonant circuit acts to impede the flow of the 20 KHz sine wave from the 20 KHZOUT pin to the 20 KHZIN pin. During the open circuit condition, the threshold comparator 378 toggles on and asserts a power disabled signal PWRDIS to an optoisolator 398 (FIG. 13) located on the RF amplifier board 60, thereby shutting off the RF power. If the bipolar pen 38 detects a resistance preferably under 5000 ohms, the secondary winding of the transformer 368 acts to reflect the impedance back to the primary winding of the transformer 368 and lower the impedance of the parallel resonant circuit, thereby allowing the 20 KHz sine wave to pass from the 20 KHZOUT pin to the 20 KHZIN pin. The signal level is detected by a pair of diodes 380, 382 within the detector 376 which cause the comparator 378 to change state, removing the power disable signal PWRDIS and thereby allowing the RF amplifier to operate.

A time delay is internally built into the OCD 354 to allow continuous application of RF power during short periods of open circuit conditions. After approximately 0.5 seconds of open circuit detection at the bipolar pen 38, RF power is extinguished.

OPERATION/SOFTWARE

The programming or software for the microprocessor 70 is shown in detail in the flow charts of FIGS. 20a-20k. The flow charts depict the procedures which are preferably performed in order to initialize the RF generator and prepare the generator for operation. An initial check is done which initializes the variables, subroutines, program counters and registers and determines whether any errors are present in the system. Depending upon the type of error which is detected, an appropriate subroutine is referenced in order to either correct the error or to communicate the error to a user. All of the LEDs and switches located on the front panel of the RF generator are checked to ensure proper operation. In addition, a sound test and memory test are performed in order to ensure that the appropriate vocal instructions and variables stored in memory are present.

Once all parameters have been checked and verified to be in proper working condition, the RF generator is ready for operation.

It will be recognized by those skilled in the art that changes may be made to the above-described embodiment of the invention without departing from the broad inventive concept thereof. It is understood, therefore, that this invention is not limited to the particular embodiment disclosed, but is intended to cover all modifications which are within the scope and spirit of the invention as defined by the appended claims.

We claim:

1. An electrosurgical bipolar RF generator apparatus comprising a bipolar electrode, means for electronically synthesizing an aperiodic sequence of uniform width bursts of a high frequency signal, means for impressing substantially identical decaying amplitude envelopes on said bursts of a higher frequency signal, each of said envelopes having a predetermined rate of change from a preselected initial amplitude and means for applying said impressed bursts of said high frequency signal to said electrode, said electrosurgical apparatus operating in a cut mode or a coagulation mode, the improvement comprising:
 a power supply for providing a variable DC voltage;
 a coagulation waveform generator for receiving and modulating said DC voltage;
 signal driving means for driving the flow of the modulated DC voltage at a predetermined rate;
 amplifying means for receiving and amplifying said modulated DC voltage, said amplifying means comprising a plurality of drivers which are alternately driven to produce a predetermined voltage level having a predetermined impedance level; and
 converting means for converting the alternately driven plurality of drivers and modulated DC voltage to an amplified RF voltage signal;
 output means for identifying whether said amplified RF voltage signal is a cut signal or a coagulation signal as determined by an impedance requirement, said output means providing impedance matching between the amplified RF voltage signal and said bipolar electrode.

2. The electrosurgical apparatus according to claim 1, wherein said amplifying means is a bridge amplifier.

3. The electrosurgical apparatus according to claim 2, wherein the bridge amplifier is an H-type bridge amplifier.

4. The electrosurgical apparatus according to claim 2, wherein the bridge amplifier includes four drivers.

5. The electrosurgical apparatus according to claim 4, wherein each bridge amplifier driver comprises a MOSFET transistor.

6. The electrosurgical apparatus according to claim 1, wherein said output means is an RF transformer.

7. The electrosurgical apparatus according to claim 1, wherein the DC voltage signal is in the range of 0 to 225.

8. The electrosurgical apparatus according to claim 1, wherein the modulated DC voltage signal is a damped sinusoidal signal.

9. The electrosurgical apparatus according to claim 1, wherein said signal driving means drives the modulated DC voltage at a 1 MHz rate.

10. An electrosurgical bipolar RF generator apparatus comprising a bipolar electrode, means for electronically synthesizing an aperiodic sequence of uniform width bursts of a high frequency signal, means for impressing substantially identical decaying amplitude envelopes on said bursts of said high frequency signal, each of said envelopes having a predetermined rate of change from a preselected initial amplitude and means for applying said impressed bursts of said high frequency signal to said electrode, said electrosurgical apparatus operating in a cut mode or a coagulation mode, the improvement comprising:
 a high voltage power supply comprising:
  a voltage source which generates an AC voltage signal;
  converting means for converting the AC voltage signal to a DC voltage signal;
  electronic switching means for receiving the DC voltage signal;
  a flyback transformer for receiving the DC voltage signal when the electronic switching means is conducting, the flyback transformer ramping linearly while the electronic switching means is conducting;
  reference signal means for generating a reference voltage signal, said reference signal means corresponding to a desired output voltage signal;
  comparing means for comparing the ramped DC voltage signal from the flyback transformer with said reference voltage signal, said comparing means determining if said ramped DC voltage signal exceeds said reference voltage signal;
  control means for controlling said ramped DC voltage signal from said flyback transformer such that said ramped DC voltage signal is prevented from exceeding said reference voltage signal, said control means preventing said desired output voltage signal from exceeding said reference voltage signal.

11. The electrosurgical apparatus according to claim 10, wherein a change in the reference voltage signal results in a proportional change in the output voltage signal from the power supply.

12. The electrosurgical apparatus according to claim 10, wherein the reference voltage does not exceed three volts.

13. The electrosurgical apparatus according to claim 10, wherein the output voltage signal is preferably less than 225 volts.

14. The electrosurgical apparatus according to claim 10, wherein the control means comprises a pulse width modulation controller.

15. An electrosurgical bipolar RF generator apparatus comprising a bipolar electrode, means for electronically synthesizing a aperiodic sequence as a uniform width burst of a high frequency signal, means for impressing substantially identical decaying amplitude envelopes on said burst of said high frequency signal, each of said envelopes having a predetermined rate of change from a preselected initial amplitude, means for applying said impressed bursts of said high frequency signal to said electrode, the improvement to the electrosurgical apparatus comprising:
 an open circuit detector including:
  a waveform generator for producing a high frequency sinusoidal audio signal;
  buffering means for buffering the audio signal;
  voltage detecting means for detecting an output voltage signal at the bipolar electrode;
  comparing means for comparing the output voltage signal sensed at the bipolar electrode with a threshold voltage;

impedance means for impeding the flow of the audio signal if the output voltage signal from the bipolar electrode exceeds the threshold voltage; and power disabling means for disabling power to the bipolar electrode when the threshold voltage is exceeded wherein said disabling power is removed when the voltage signal no longer exceeds the threshold voltage.

16. The electrosurgical apparatus according to claim 15, wherein said high frequency sinusoidal audio signal is 3 volts peak to peak and 20 KHz.

17. The electrosurgical apparatus according to claim 15, further comprising signal level detecting means for detecting the signal level of the output voltage signal.

* * * * *